(12) United States Patent
Kashiwaba et al.

(10) Patent No.: US 6,770,630 B2
(45) Date of Patent: Aug. 3, 2004

(54) NARINGENIN DERIVATIVES AND USE THEREOF

(75) Inventors: Kouichi Kashiwaba, Inashiki-gun (JP); Norihiko Tomooka, Tsukuba (JP); Duncan A. Vaughan, Tsukuba (JP); Akito Kaga, Tsukuba (JP); Hiroshi Ono, Tsukuba (JP); Mayumi Kameyama, Kashiwa (JP); Mituru Yoshida, Tsukuba (JP)

(73) Assignees: Japan Science and Technology Corporation, Kawaguchi (JP); National Institute of Agrobiological Sciences, Tsukuba (JP); National Food Research Institute, Tsukuba (JP)

( * ) Notice: Subject to any disclaimer, the term of this patent is extended or adjusted under 35 U.S.C. 154(b) by 5 days.

(21) Appl. No.: 10/145,117

(22) Filed: May 15, 2002

(65) Prior Publication Data
US 2003/0109462 A1 Jun. 12, 2003

(30) Foreign Application Priority Data
Oct. 30, 2001 (JP) ........................................ 2001-331795

(51) Int. Cl.[7] ........................ A01N 43/04; A01N 57/00; A01N 43/16; C07H 17/00
(52) U.S. Cl. ........................ 514/27; 514/23; 514/456; 536/8; 549/403
(58) Field of Search ........................ 514/456; 536/8; 549/403

(56) References Cited

PUBLICATIONS

Velozo, et al "Constituents from the roots of *Bowdichia virgilioides*", Fitoterapia, 1999, vol. 70, pp 532–535.*
Budzianowski, J. et al "6–C–Glucosylnaringenin From *Tulipa gesneriana*", Phytochemistry, 1978, vol. 17, pp 2044.*

* cited by examiner

*Primary Examiner*—James O. Wilson
*Assistant Examiner*—Ganapathy Krishnan
(74) *Attorney, Agent, or Firm*—Oblon, Spivak, McClelland, Maier & Neustadt, P.C.

(57) ABSTRACT

A naringenin derivative of the general formula I:

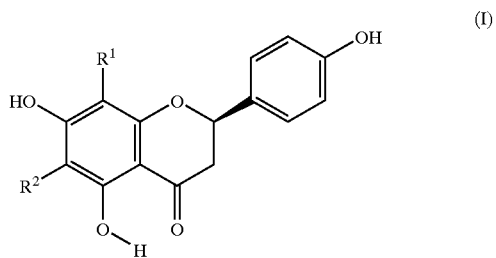

where $R^1$ and $R^2$ each represents either a hydrogen atom or β-D-glucosyl group, and but both $R^1$ and $R^2$ are not identical.

10 Claims, 25 Drawing Sheets

NARINGENIN DERIVATIVES AND USE THEREOF

FIELD OF THE INVENTION

The invention described here relates to novel naringenin derivatives and use thereof. More particularly, it relates to novel naringenin derivatives by which food pulse seeds such as azuki bean (*Vigna angularis*), cowpea (*Vigna unguiculata*), and mungbean (*Vigna radiata*) can effectively be protected from feeding by bean weevils and to insecticidal compositions comprising the novel naringenin derivatives as active components.

BACKGROUND OF THE INVENTION

Control of crops from injurious insects is practiced to ensure stability of the yield and the quality of harvested products.

From the early 20th century, such synthetic insecticides as organic chlorides or organic phosphorus compounds, have been employed in controlling such injurious insects, and have greatly contributed to agricultural production.

In recent years, however, environmental protection or safety has resulted in a decline in use of synthetic insecticides.

As the amount of synthetic insecticides used increases, it has been reported that insects acquire chemical tolerance to these insecticides. Therefore, alternative new technologies are desired to replace synthetic insecticides.

In general, insecticides derived from naturally occurring products are considered to be less harmful to the environment.

In particular, a variety of natural compounds of plant origin have been used as insecticides, these include such compounds as pyrethroids. Flavonoid glycosides are a group of compounds produced by plants. The flavonoids are considered to contribute to antibacterial activity, enzyme inhibition, prevention from feeding injury by insects, and hormone action. Though all their functions in plants have yet to be elucidated.

The flavonoid, 6-C-β-D-glucosyl-luteolin has an insecticidal effecton larva of giant tobacco budworm (*Heliothis obsoleta* Fabricius). There have been no reports of the effect of flavonoids on bean weevils.

Bean weevils are small beetles that are distributed in the tropical or subtropical zone. The bean weevils include azuki bean weevil (*Callosobruchus chinensis*) and cowpea weevil (*Callosobruchus maculatus*), and they feed on the seeds of azuki bean, rice bean (*Vigna umbellata*), cowpeas, and mung bean. Among them, cowpea weevil, which is distributed in Africa and Southeast Asia, are a major grain pest could spread outside the tropics if global warming continues.

Adult bean weevils fly into bean fields, where they lay eggs on young bean pods. The hatched larvae eat into the seeds, and later emerge from bean seeds after harvesting in seed storage areas. The emerged adult bean weevils lay eggs on the beans in storage faculties. Thus, as the generations of bean weevil are repeated, damage to seeds increases.

The life cycle of bean weevils can speed up when the environmental conditions are good, and thus cause great damage to beans in storage by feeding injury. Therefore, the protection of beans in the field from adult bean weevils has long been performed by scattering of agrochemicals or by treatment with chemicals after harvesting.

It is very difficult, however, to exterminate all the larvae of bean weevils invading bean seeds since the adults have high mobility. Extermination of the larvae which have invaded into the bean seeds is also difficult. To date, damage by bean weevils remains a serious problem despite control measures.

Therefore, there is a worldwide need for new and effective preventive methods.

SUMMARY OF THE INVENTION

The purpose of the invention described here is to provide novel naringenin derivatives of natural (plant) origin, having insect resistance, wherein it is possible to solve the above-mentioned problems and control bean weevils which cause feeding injury to grain legume seeds during ripening in the field and in storage. The purpose of the invention is also to provide insecticidal compositions comprising the novel naringenin derivatives as active components.

The present inventors worked assiduously to solve the above-mentioned problems and found that an edible bean native to Japan, i.e., rice bean (*Vigna umbellata*), exhibits a high level of insecticidal action (insect resistance) to be an weevils including azuki bean weevil and cowpea weevil. The rice bean was selected from 500 strains of leguminous seeds in the National Institute of Agrobiological Sciences, Japan, germplasm collections.

The seeds of rice bean contain an active component having an insecticidal action (insect resistance) to bean weevils. In addition, since the seeds of rice bean are edible, the active component contained therein is considered to be safe for humans in the concentrations they are present in rice bean.

In order to elucidate the factor(s) related to resistance in rice bean to bean weevils, the present inventors used various methods and extraction solvents to isolate an insecticidally active substance from the seed powder of rice bean. They found novel naringenin derivatives that have not yet been described in the literature. The invention was completed based on these findings.

According to the 1st aspect, the present invention provides a novel naringenin derivative of the general formula (I):

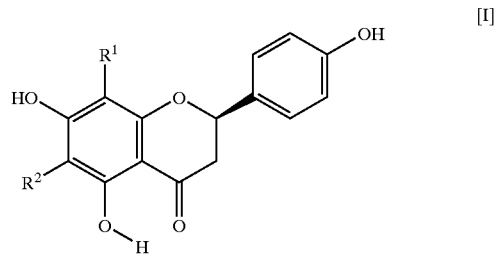

(wherein $R^1$ and $R^2$ each represents either a hydrogen atom or β-D-glucosyl group, but $R^1$ and $R^2$ cannot both have the same chemical structure).

Next, according to the 2nd aspect the invention provides an insecticidal composition comprising the naringenin derivative according to the 1st aspect as an active component.

Moreover, according to the 3rd aspect the invention provides an insecticidal composition according to the 2nd aspect, wherein the insecticidal composition is injurious to insects feeding on legume seeds.

Moreover, according to the 4th aspect the invention provides an insecticidal composition according to the 3rd aspect, wherein the injured legume seed eating insects are bean weevils.

DETAILED DESCRIPTION OF THE INVENTION

Figure 1:
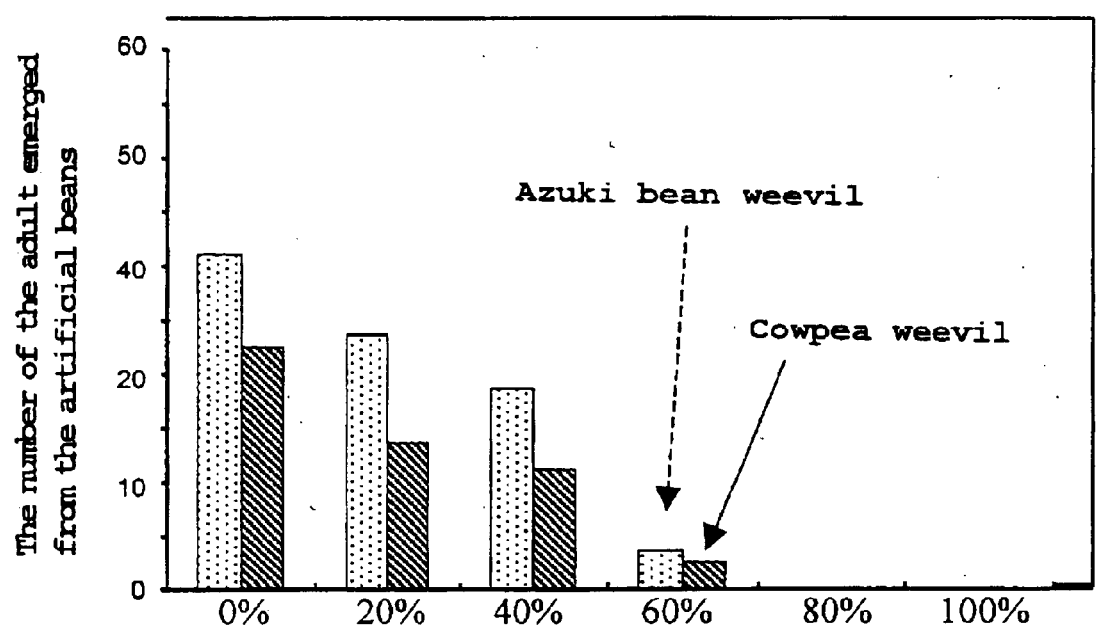
FIG. 1 shows the number of the adults emerged from the artificial beans prepared by mixing rice bean seed powder with powder of azuki bean seeds that are susceptible to bean weevil.

The following show the mode for carrying out the invention.

The invention according to the 1st aspect provides a novel naringenin derivative represented by the above general formula (I).

In the above formula, $R^1$ and $R^2$ each represents either a hydrogen atom or β-D-glucosyl (β-D-Glc) group, but $R^1$ and $R^2$ cannot both have the same chemical structure.

In the novel naringenin derivatives of the above general formula (I), accordingly, 8-C-β-D-glucosyl-(R)-naringenin represented by formula (II):

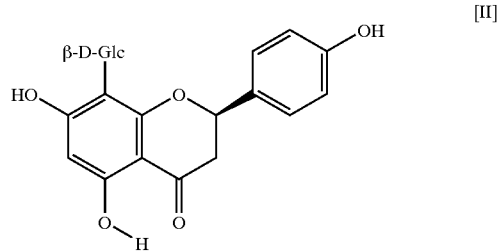

is included.

Moreover, in the novel naringenin derivatives of the above general formula (I), 6-C-β-D-glucosyl-(R)-naringenin represented by formula (III):

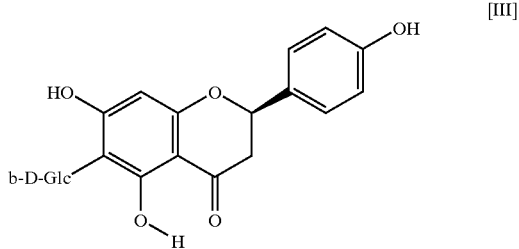

is included.

The naringenin derivatives of the above general formula (I) are novel compounds which have not previously been described in any literature. Consequently, the action of these novel naringenin derivatives with respect to insecticidal action (insect resistance) to bean weevils has not been reported.

The naringenin derivatives of the above general formula (I) may be obtained by extracting the seed powder of edible rice bean with aqueous methanol.

Among the naringenin derivatives of the above general formula (I), in obtaining 8-C-β-D-glucosyl-(R)-naringenin represented by formula (II), first the seeds of rice bean are pulverized and the resulting seed powder of rice bean is extracted with 85% methanol aqueous solution. The resulting extract is then condensed, partitioned among water-saturated hexane, ethyl acetate, and water-saturated butanol. The butanol layer in which an insecticidal activity to bean weevils is found is condensed, adsorbed on silica gel, and eluted with a mixture of hexane/ethyl acetate and then with a mixture of ethyl acetate/methanol. The condensed fraction of ethyl acetate/methanol (8:2) in which an insecticidal activity to bean weevils is found is purified by low pressure liquid chromatography. Thereafter, the most active condensed fraction is purified by high performance liquid chromatography (HPLC) to yield a peak showing insecticidal activity to bean weevils. This peak is further purified to yield the novel compound 8-C-β-D-glucosyl-(R)-naringenin which has not previously been described in the literature. The structure was determined by means of MS, CD and NMR.

This novel compound 8-C-β-D-glucosyl-(R)-naringenin shows insecticidal activity only to azuki bean weevils. The rice bean seeds, however, exhibit a high insecticidal activity to both azuki bean weevil and cowpea weevil.

Therefore, the inventors considered that another compound must exist, which had an insecticidal activity to bean weevil in addition to the novel compound 8-C-β-D-glucosyl-(R)-naringenin, and they applied another chemical separation method.

It was found in the course of purification the use of a hydrophilic vinyl polymer resistant to organic solvents in place of silica gel permitted separation of an insecticidally active compound against cowpea weevils. By this means, the novel compound 6-C-β-D-glucosyl-(R)-naringenin of the above formula (III), which has not previously been described in any literature, was obtained.

Therefore, in order to isolate the novel compound 6-C-β-D-glucosyl-(R)-naringenin of the above formula (III), first the seeds of rice bean are pulverized and extracted with 85% methanol aqueous solution. The resulting extract is condensed and partitioned into water-saturated hexane and water-saturated butanol. The butanol layer in which is recognized to have insecticidal activity to bean weevils is condensed and purified by low pressure liquid chromatography using a column packed with a hydrophilic vinyl polymer resistant to organic solvents. The most active condensed fraction is purified by HPLC. The peak fraction that shows the insecticidal activity to azuki bean weevils and cowpea weevils is purified to yield 6-C-β-D-glucosyl-(R)-naringenin of the above formula (III). The structure was determined by means of MS, CD and NMR.

As mentioned above, the naringenin derivatives of the general formula (I) are considered to be safe for human consumption in the quantity they are present in rice bean because rice beans have been consumed by humans for a long time and no ill effects have been reported.

The novel naringenin derivatives of the invention according to the 1st aspect are as described above.

Next, the invention according to the 2nd aspect provides an insecticidal composition comprising the naringenin derivative according to the 1st aspect as an active component.

Specifically, the naringenin derivatives according to the 1st aspect include 8-C-β-D-glucosyl-(R)-naringenin of formula (II) and 6-C-β-D-glucosyl-(R)-naringenin of formula (III). In the invention according to the 2nd aspect, however, these two novel compounds can be used in combination.

Additionally, the insecticidal compositions of the invention according to the 2nd aspect may be those containing the naringenin derivative according to the 1st aspect as an active component. The composition accordingly may be used in combination with a so far known insecticidal substance as far as it does not spoil the purpose of the invention.

Such insecticidal compositions of the invention according to the 2nd aspect are particularly useful as insecticidal compositions for injurious insects to legume seeds as described in the 3rd aspect.

In this connection, the injurious insects to legume seeds include bean weevils as described in the 4th aspect.

The insecticidal compositions of the invention according to the 2nd aspect have specific and selective insect resistance to bean weevils such as azuki bean weevil and cowpea weevil particularly among insects injurious to legume seeds.

In the insecticidal compositions of the invention according to the 2nd aspect, it is possible effectively to prevent injurious insects to grains such as bean weevils from feeding on food pulse seeds such as azuki bean, cowpeas, and munbeans.

The insecticidal compositions of the invention according to the 2nd aspect, in view of an invading route of a chemical into the body of an injurious insect, belong basically to a category of stomach poisons of insecticides. The injurious insects which have eaten the compositions result in intoxication and finally in death. Thus, the prevention of insect reproduction and feeding is realized. In the insecticidal compositions of the invention according to the 2nd aspect, there is no limitation in embodiment of the use as insecticides. In order to promote the eating by the injurious insects, it is appropriate, for example, to make the compositions in a form of artificial beans imitating natural beans.

ADVANTAGE OF THE INVENTION

The naringenin derivatives described in this invention concerning the 1st aspect are novel compounds that have not yet been described in any literature. The derivatives are useful as insecticides (protection against bean weevils) since they prevent bean weevils effectively from feeding on seeds of beans during maturation in the field and storage.

The insecticidal compositions of the invention concerning the 2nd aspect, which comprise the novel naringenin derivatives as described in the 1st aspect as active components, have insect resistance to prevent bean weevils effectively from feeding the seeds of beans during maturation in the field and storage.

Moreover, the active components in the insecticidal compositions of the invention concerning the 2nd aspect may be said to be naturally occurring (plant) products, which have not been produced by organic syntheses, since they are components contained in edible rice bean seeds. Thus, they have been consumed by humans with no reported ill effect.

The insecticidal compositions of the invention concerning the 2nd aspect show specific and selective effect on bean weevils such as azuki bean weevils and cowpea weevils among injurious insects to seeds.

The insecticidal compositions of the invention concerning the 2nd aspect can prevent bean weevils effectively from feeding on the seeds of food pulses such as azuki bean, cowpeas, and mungbean.

EXAMPLES

The followings illustrate the working examples of the invention, but the invention is not limited by these examples. Experiment 1 [Test for Insecticidal Activity of the Seed Powder of Rice Bean]

Since it was observed that the larvae of bean weevils that had eaten the kernel of edible rice bean resulted in death, the following test was conducted to confirm the insecticidal activity of the seeds (cotyledon) of rice bean against bean weevils. Thus, the larvae of bean weevils were fed with artificial beans containing the seed powder of rice bean.

(1) Rice Bean

Rice bean (*Vigna umbellata*) of Japanese origin was used as raw material.

(2) Bean Weevils

Two species of bean weevils, i.e., azuki bean weevil (*Callosobruchus chinensis*) and cowpea weevil (*C. maculatus*) were employed. Cowpea weevil was obtained from Kasetsart University, Thailand, under an import license from the Plant Quarantine Office of Japan and subcultured.

These two species of bean weevils were cultured in the same way. In a 9 cm Petri dish containing 300 mungbean seeds, was placed ten adults of bean weevil and egg production was induced. After egg production, the adults were removed and cultured in a thermostatically controlled incubator at 60% humidity and 30° C. After 25 to 30 days from the egg production, the adults emerged. The emerged adults were used in the test for insecticidal activity.

(3) Preparation of Artificial Beans; Mungbean 100% (Control)

In order to identify an insecticidally active substance, the bean weevils have to be cultured on artificial feed. Therefore, artificial beans (artificial feed) were prepared from the cotyledon powder of mungbean do not affect bean weevil growth and reproduction, and the growth of bean weevils was observed thereon. To 1 g of the cotyledon powder of mungbean was added a small quantity of water to make bean-like solid material (about 0.25 g), which was freeze-dried. This material was called artificial bean (mungbean 100%) and used in the test.

The artificial beans (mungbean 100%) were placed in a 9 cm Petri dish, on which was then put the adults shortly after their emergence and eggs were laid on the artificial seeds. The culture environment was fixed at a temperature of 30° C. and a humidity of 60%. After a lapse of 25 to 30 days from the egg production, the adults normally emerged from the artificial beans (mungbean 100%). Thus, it became clear that the bean weevils can utilize the artificial beans for their egg production and emergence, and it was confirmed that the artificial beans are useful in a test of insecticidal activity for bean weevils.

(4) Preparation of Artificial Beans Containing the Seed Powder of Rice Bean and Determination of Insecticidal Activity One artificial seed each of artificial beans in this test was placed in a 9 cm Petri dish, on which the adults of azuki bean weevils or cowpea weevils shortly after the emergence were put and induced to lay eggs. After egg production, the adults were cultured in an incubator fixed at 30° C. and 60% humidity. The number of eggs laid on the artificial beans was recorded, and the number of the adults that emerged from the artificial beans was continuously recorded for up to 50 days after the egg production to calculate the rate of emergence. The artificial beans on which no emergence was recorded by the 50th day after eggs were laid were split with a pair of forceps and checked as to whether there was any larvae in the artificial seed. This experiment, the insecticidal test on the artificial beans, was repeated 4 times.

FIG. 1 shows the number of the adults which emerged from artificial beans prepared by mixing seed powder of rice bean in various proportions. In FIG. 1, the dotted bars indicate the results for azuki bean weevil and the hatched bars the results for cowpea weevil.

From FIG. 1, it is apparent that the emergence of two species of bean weevils have been inhibited completely on the artificial beans containing 100% rice bean seed powder and those containing 80% rice bean seed powder+20% mungbean seed (cotyledon) powder.

On the basis of these results, the total activity (units) and specific activity of the rice bean seed powder were calculated.

In this case, the concentration of the rice bean seed powder required for exhibiting insecticidal activity (emergence rate 0%) on the above artificial beans was determined and regarded as the minimum lethal concentration. The value represented by the weight (g) of the artificial beans which can be prepared from the total weight of rice bean seed powder according to the minimum lethal concentration was regarded as the total activity of the rice bean seed powder. (The value derived by dividing the total weight of rice bean seed powder by the minimum lethal concentration)

Moreover, the total activity for 1 g of the rice bean seed powder was calculated as specific activity (units/g).

In this test, the emergence of two species of bean weevils was inhibited completely on the artificial beans containing 100% rice bean seed powder and those containing 80% rice bean seed powder+20% mungbean seed (cotyledon) powder (see FIG. 1). So, it is understood that the minimum lethal concentration of rice bean seed is 80%.

The total activity of the rice bean seed powder can be calculated from this result as a standard. Since 1000.0 g of the rice bean seed powder can be formulated into 1250.0 g of the artificial beans in which amount the bean weevils may be killed, it is apparent that the total activity is 1250.0 units. In this connection, the specific activity is 1.3 units/g. Table 1 shows the results.

Since the larvae of bean weevils that have eaten the artificial beans comprising a mixture of rice bean seeds die, it is apparent that the rice bean seeds have an insecticidal activity to bean weevils.

From these results, it was considered that rice bean contain an effective component exhibiting insecticidal activity to bean weevils. Therefore, separation of an insecticidal substance or substances from the seeds of rice bean was carried out as shown in Examples 1 and 2.

Example 1

[Production of 8-C-β-D-glucosyl-(R)-naringenin]

Figure 2:
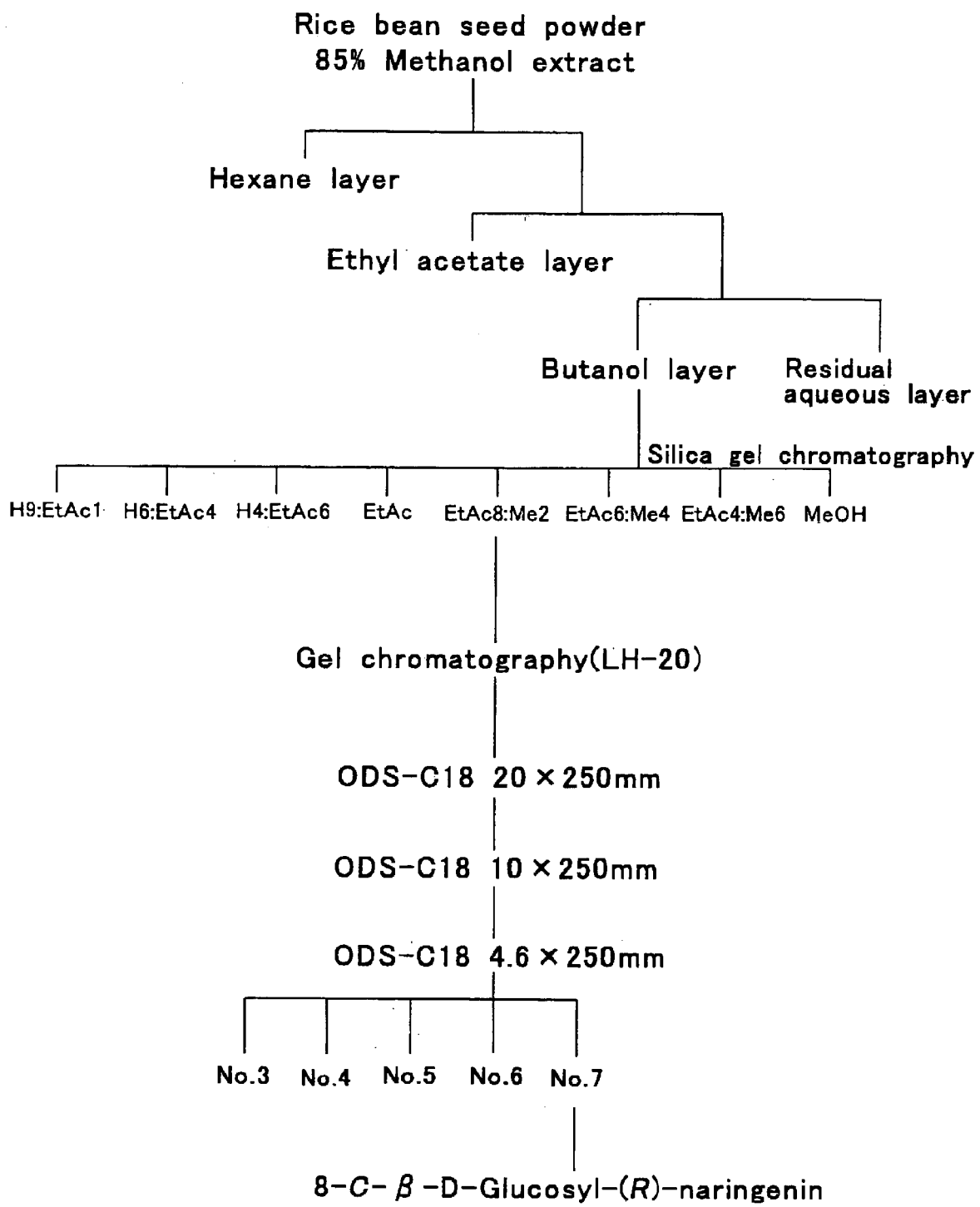
FIG. 2 shows a procedure for separation and purification of 8-C-β-D-glucosyl-(R)-naringenin from the seeds of rice bean.

A substance having insecticidal activity to bean weevils was separated and purified from the seeds of rice bean based on the insecticidal activity to bean weevils. FIG. 2 shows a procedure for separation and purification of the substance.

Insecticidal activity was observed by calculating total activity and specific activity under the same conditions and following the same procedure as in Experiment 1, except that the extract obtained in each step of purification was used in place of the seed powder of rice bean.

In this connection, the total activity of the extract obtained during each step of purification was shown as a ratio to the total activity of the seed powder of rice bean obtained in Experiment 1. Thus, the ratio was indicated as a percentage, from which the yield was calculated.

(1) Extraction with Methanol

To the seed powder of rice bean was added 10 l of 85% methanol (methanol:water=85:15) and extracted continuously for 48 hours (4° C.). The extract was filtered to give 9.5 l of supernatant. This operation was repeated 3 times to obtain about 28 l of methanol extract from a total of 3000 g the seed powder.

For the methanol extract, the total activity, specific activity and yield were calculated in the same manner as in Experiment 1. Table 1 shows the results.

From Table 1, it is apparent that the methanol extract is more active than the 100% seed powder of rice bean in insecticidal activity.

(2) Partition into Each Solvent

The extract was condensed and partitioned into water-saturated hexane, ethyl acetate, and water-saturated butanol.

Then, the test for insecticidal activity was carried out using the resulting partitioned water-saturated hexane layer, partitioned ethyl acetate layer, and partitioned water-saturated butanol layer, and the residual aqueous layer, respectively.

Figure 3:
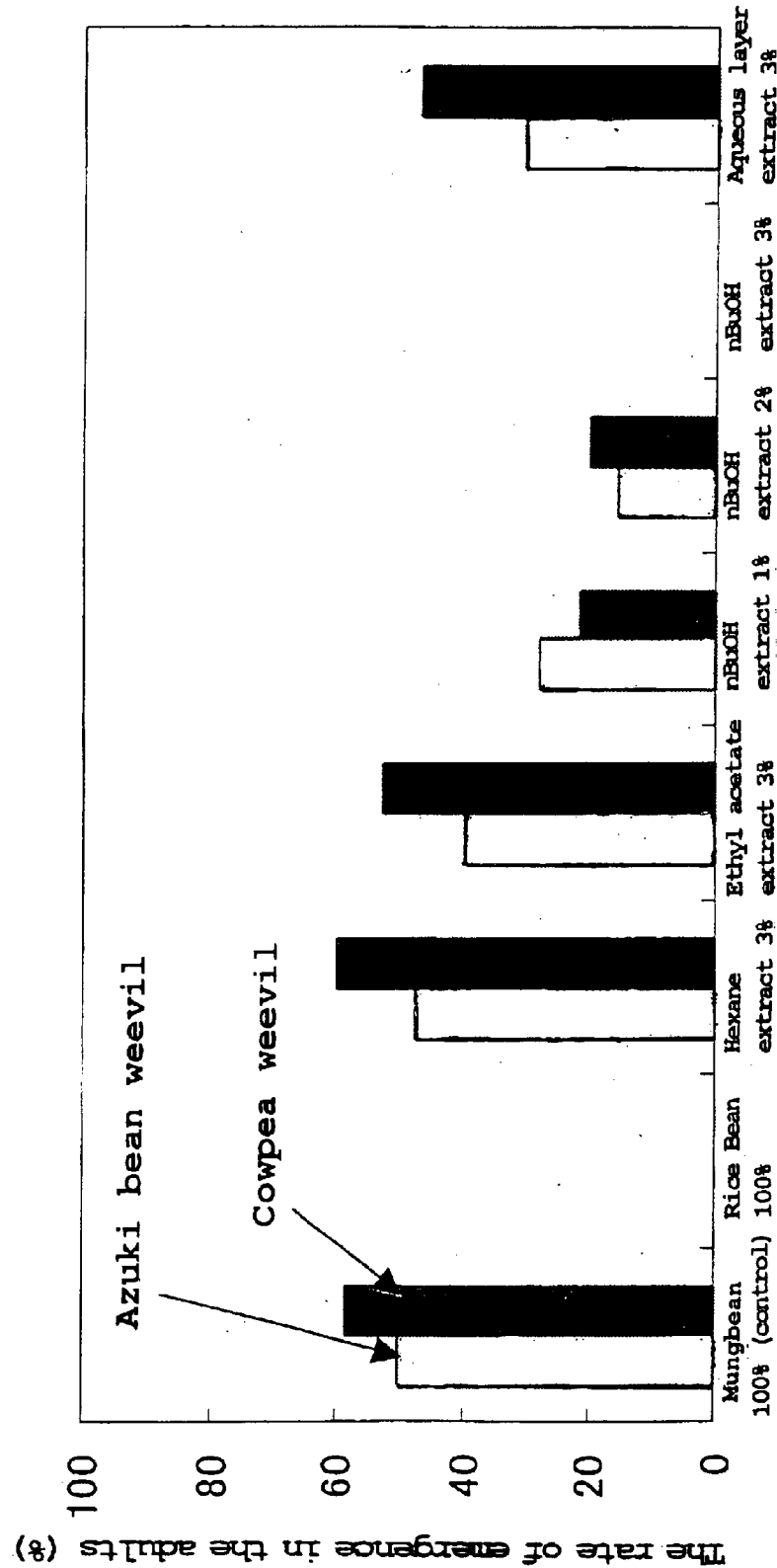
FIG. 3 shows the rate of emergence of adults on the artificial beans prepared by mixing the extracts with a variety of solvents.

The rate of emergence was confirmed in the same manner as in Experiment 1, except that the artificial beans containing 3% of the partitioned hexane layer, 3% of the partitioned ethyl acetate layer, 1%, 2% or 3% of the partitioned butanol layer, or 3% of the residual aqueous layer, respectively, were used in place of the seed powder of rice bean. FIG. 3 shows the results of the rate of emergence on the artificial beans containing the respective extracts. In FIG. 3, the white bar indicates the results for azuki bean weevils and the black bar for cowpea weevils, respectively.

As seen apparently from FIG. 3, the rates of emergence on the artificial beans containing the partitioned hexane layer, the partitioned ethyl acetate layer, and the residual aqueous layer, respectively, were high. On the other hand, the rate of emergence on the artificial beans containing the partitioned butanol layer was low for both of species of bean weevils tested. The rate of emergence on the artificial beans containing 3% of the partitioned butanol layer was 0%, and the minimum lethal concentration was found to be 3%, accordingly.

Then, for the artificial beans containing the partitioned butanol layer, the total activity and specific activity were calculated in the same manner as in Experiment 1. Further, the yield was calculated. Table 1 shows these results.

As is clearly seen from Table 1, the total activity was lower than those of the methanol extract and the specific activity was higher than those of the methanol extract.

From the above results, insecticidal activity to two species of bean weevils was recognized to be in the partitioned butanol layer, which was then subjected to the following purification procedure.

(3) Separation by Silica Gel Column Chromatography

The partitioned butanol layer was condensed and purified by silica gel column chromatography. The column was eluted with hexane/ethyl acetate (90:10), hexane/ethyl acetate (60:40), hexane/ethyl acetate (40:60) and ethyl acetate, and then with ethyl acetate/methanol (80:20), ethyl acetate/methanol (60:40), ethyl acetate/methanol (40:60) and methanol.

The respective eluates were condensed and confirmed to have insecticidal activity to bean weevils.

The test for the insecticidal activity was carried out in the same manner as in Experiment 1. As a result, it was confirmed that the condensate of the eluate with ethyl acetate/methanol (80:20) had the insecticidal activity to azuki bean weevils. Table 1 shows the results of the total activity and specific activity to azuki bean weevils and the yield in the condensate of the ethyl acetate/methanol (80:20) eluate.

(4) Separation by Gel Chromatography

The condensate of the ethyl acetate/methanol (80:20) eluate was dissolved in a small quantity of 10% methanol (methanol/water=10:90) and separated on an LH-20 packed column (2×120 cm) for gel chromatography.

The column was eluted with 10% methanol as a starting solvent and in a linear concentration gradient up to 100% methanol for 1400 minutes (flow rate 2 ml/min; column temperature 20° C.). The eluates were collected every 10 minutes after addition of a sample. The respective fractions collected were condensed under reduced pressure, and freeze-dried.

The insecticidal activity to azuki bean weevils was confirmed in the respective fractions.

The above respective fractions were mixed to prepare the artificial beans, for which the insecticidal test was carried out in the same manner as in Experiment 1 to calculate the emergence rate, total activity, and specific activity. As a result, a fraction showing the insecticidal activity to azuki bean weevils was obtained. Table 1 shows the results of the total activity and specific activity and the yield in the fraction in which the insecticidal activity to azuki bean weevils has been recognized.

(5) Separation by HPLC

The fraction in which the insecticidal activity to azuki bean weevils was recognized was purified by HPLC (Shimadzu). The columns Sensyu Kagaku ODS-C18 (20× 250 mm and 10×250 mm) and Shiseido ODS-UC18 (4.6× 250 mm) were employed. The absorbance was measured at 200 to 400 nm.

Figure 4:
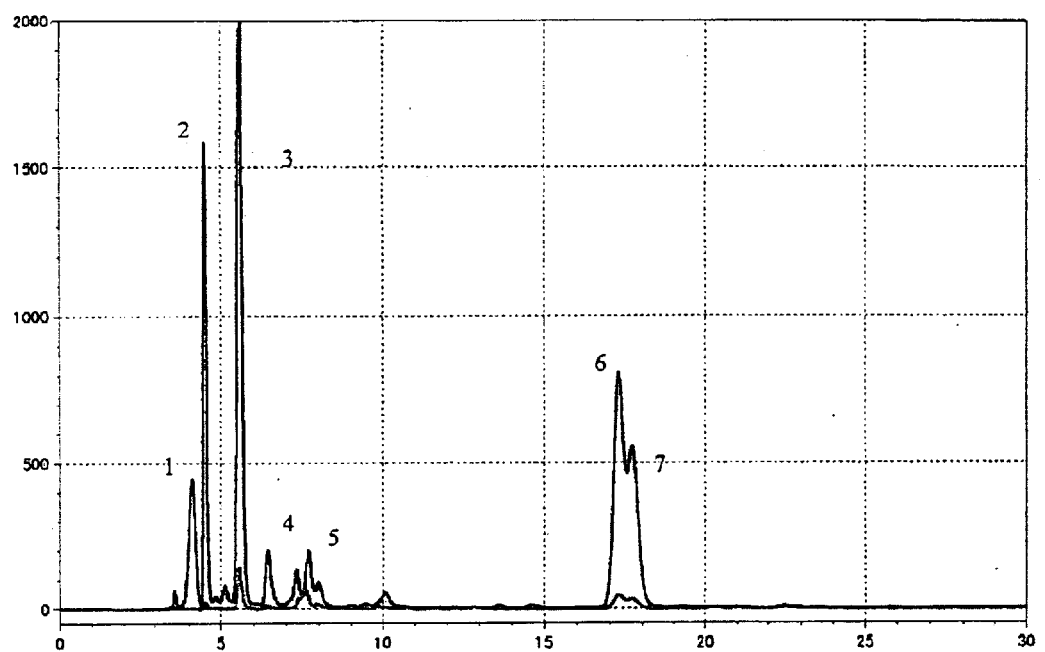
FIG. 4 shows the result of HPLC.

The fraction in which the insecticidal activity to azuki bean weevils was recognized was analyzed with the column ODS-UC18 (4.6×250 mm) at a flowrate of 0.8 ml/m in and a column temperature of 40° C. using 20% acetonitrile (acetonitrile/water=20:80) as eluent. FIG. 4 shows the results of HPLC. As seen from FIG. 4, 7 peaks (Nos. 1 to 7) were detected.

The respective peak fractions were collected and confirmed to have insecticidal activities. The insecticidal test was carried out in the same manner as in Experiment 1, except that the artificial beans were prepared by mixing the respective peak fractions. Thus, the rate of emergence, total activity, and specific activity were calculated.

As a result, the insecticidal activity to azuki bean weevils was recognized at the peaks appearing at 17 to 18 minutes of the elution time (Nos. 6 and 7). Table 1 shows the results of the total activity and specific activity and the yield in the peak fractions (Nos. 6 and 7) at 17 to 18 minutes.

The peak fractions (Nos. 6 and 7) at 17 to 18 minutes of elution time on ODS-C18 columns (20×250 mm and 10×250 mm) were collected. Since these fractions were comprised of two peaks, the collected peak fractions were freeze-dried and separated by means of a column Shiseido ODS-C18 (4.6×250 mm).

Figure 5:
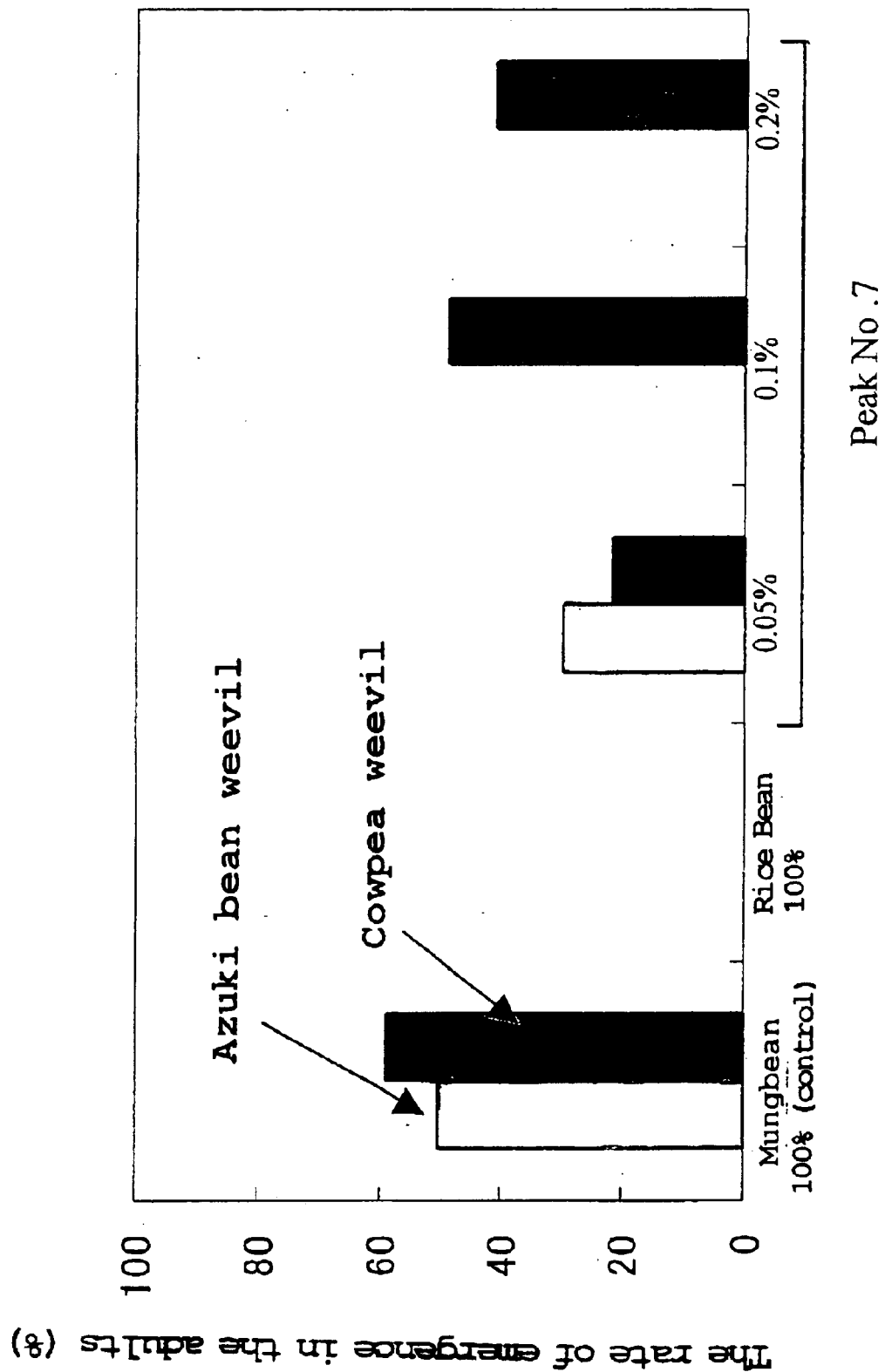
FIG. 5 shows the rate of emergence of adults on the artificial beans prepared by mixing the chemical represented in the 7th (No. 7) peak.

The insecticidal activity was confirmed in the 7th peak (No. 7). The insecticidal test was carried out in the same manner as in Experiment 1 to calculate the rate of emergence, except that the artificial beans were prepared by mixing 0.05%, 0.1%, or 0.2% of the 7th (No. 7) peak fraction. FIG. 5 shows the result of the rate of emergence on the artificial beans containing the 7th peak. In FIG. 5, the white bar indicates the results for azuki bean weevils and the black bar for cowpea weevils, respectively.

As is seen clearly from FIG. 5, the rate of emergence on the artificial beans containing the 7th peak extract was low for azuki bean weevils. On the artificial beans containing 0.1% or 0.2% of the 7th peak, however, the rate of emergence in azuki bean weevils was 0%. Thus, the minimum lethal concentration was confirmed to be 0.1%.

In the same manner as in Experiment 1, the total activity and specific activity were calculated for the artificial beans containing the 7th (No. 7) peak extract. Further, the yield was calculated. The results are shown in Table 1.

TABLE 1

Insecticidal activity of the extract in each step of purification

| Purification step | Extract (g) | Total activity (units) | Specific activity (units/g) | Yield (%) |
|---|---|---|---|---|
| Rice bean seed powder | 1000.0 | 1250.0 | 1.3 | 100.0 |
| Methanol extract | 51.5 | 858.3 | 16.7 | 68.7 |
| Butanol partition layer | 15.4 | 513.3 | 33.0 | 41.1 |
| Silica gel chromatography (EtOAc/MeOH = 80:20) (Condensate) | 0.33 | 41.3 | 125.0 | 3.3 |
| Low pressure liquid chromatography (Active fraction) | 0.06 | 15.0 | 250.0 | 1.2 |
| HPLC (6th and 7th peaks) | 0.006 | 6.0 | 1000.0 | 0.5 |
| HPLC (7th peak) | 0.002 | 2.0 | 1000.0 | 0.16 |

As seen from Table 1, in the 7th (No. 7) peak, the total activity is low, and the specific activity is high.

From the above results, since the insecticidal activity was recognized in the 7th peak, this peak fraction was analyzed.

Figure 6:
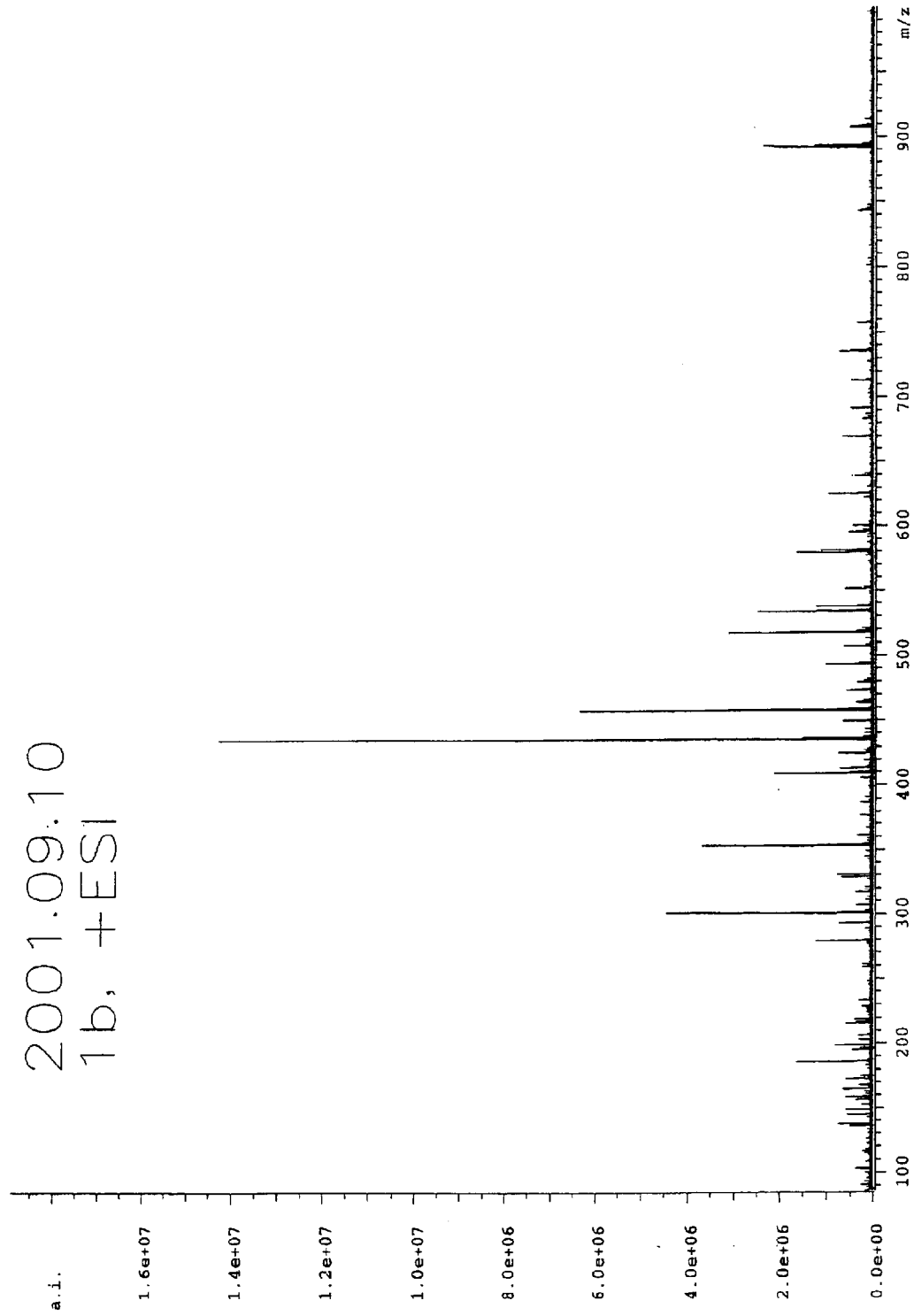
FIG. 6 shows the result of mass spectroscopic analysis (mass spectrum) of the compound contained in the lyophilizate of the 7th (No. 7) peak.
Figure 7:
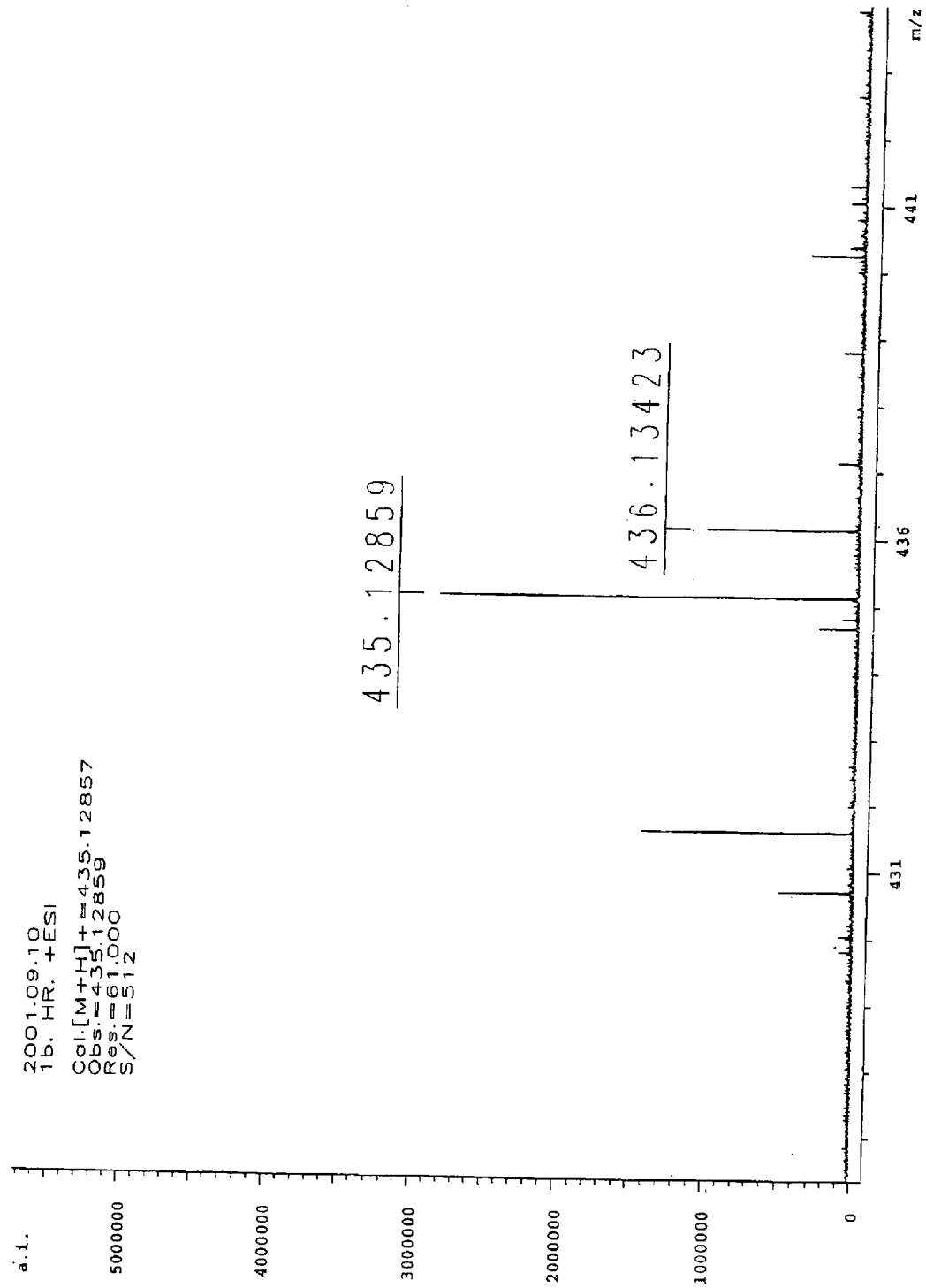
FIG. 7 shows the result of precision mass spectroscopic analysis (mass spectrum: [M+H]$^+$) of the compound contained in the lyophilizate of the 7th (No. 7) peak.
Figure 8:
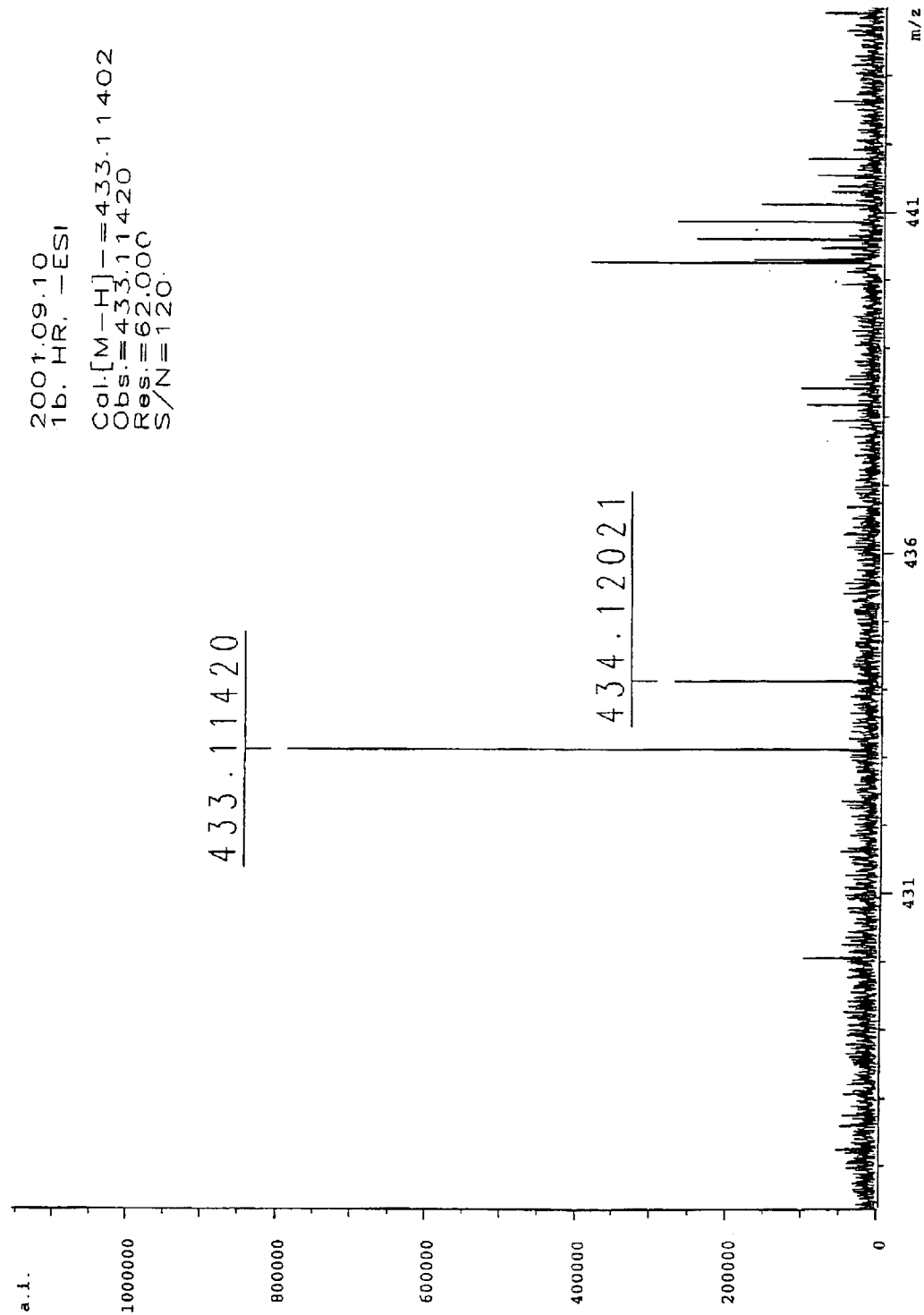
FIG. 8 shows the result of precision mass spectroscopic analysis (mass spectrum: [M–H]$^-$) of the compound contained in the lyophilizate of the 7th (No. 7) peak.

The compound contained in the lyophilizate of the 7th peak fraction was analyzed by the Fourier transformation ion cyclotron resonance mass spectrometry (FTICR-MS). The results of mass spectrometric analyses are shown in FIG. 6 (mass spectra). The results of precision mass spectrometric analyses (precision mass spectra) are shown in FIGS. 7 and 8. As shown in FIGS. 7 and 8, [M+H]$^+$ was observed at m/z 435.12859, and [M−H]$^−$ at m/z 433.11420. When regarded as $C_{21}H_{23}O_{10}$, [M+H]$^+$ is m/z435.12857, and [M−H]$^−$ is m/z 433.11402.

Figure 9:
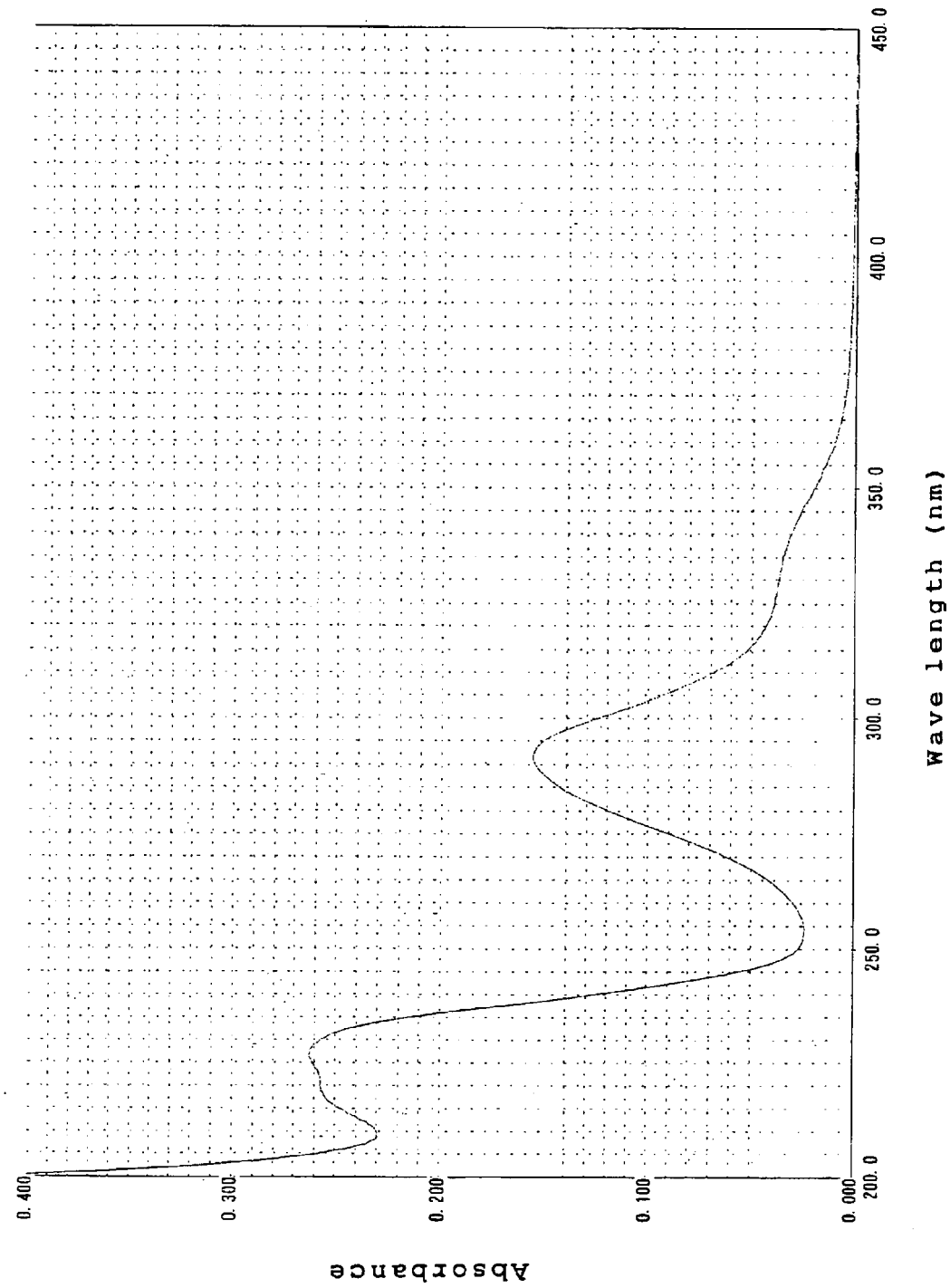
FIG. 9 shows a UV spectrum of the compound contained in the lyophilizate of the 7th (No. 7) peak.

FIG. 9 shows a UV spectrum of the compound contained in the lyophilizate of the 7th (No. 7) peak. The strong absorption band at around 290 nm and the weak absorption band at around 330 nm are attributed to π→π* and n→π* transitions, respectively, in the flavanone skeleton.

Figure 10:
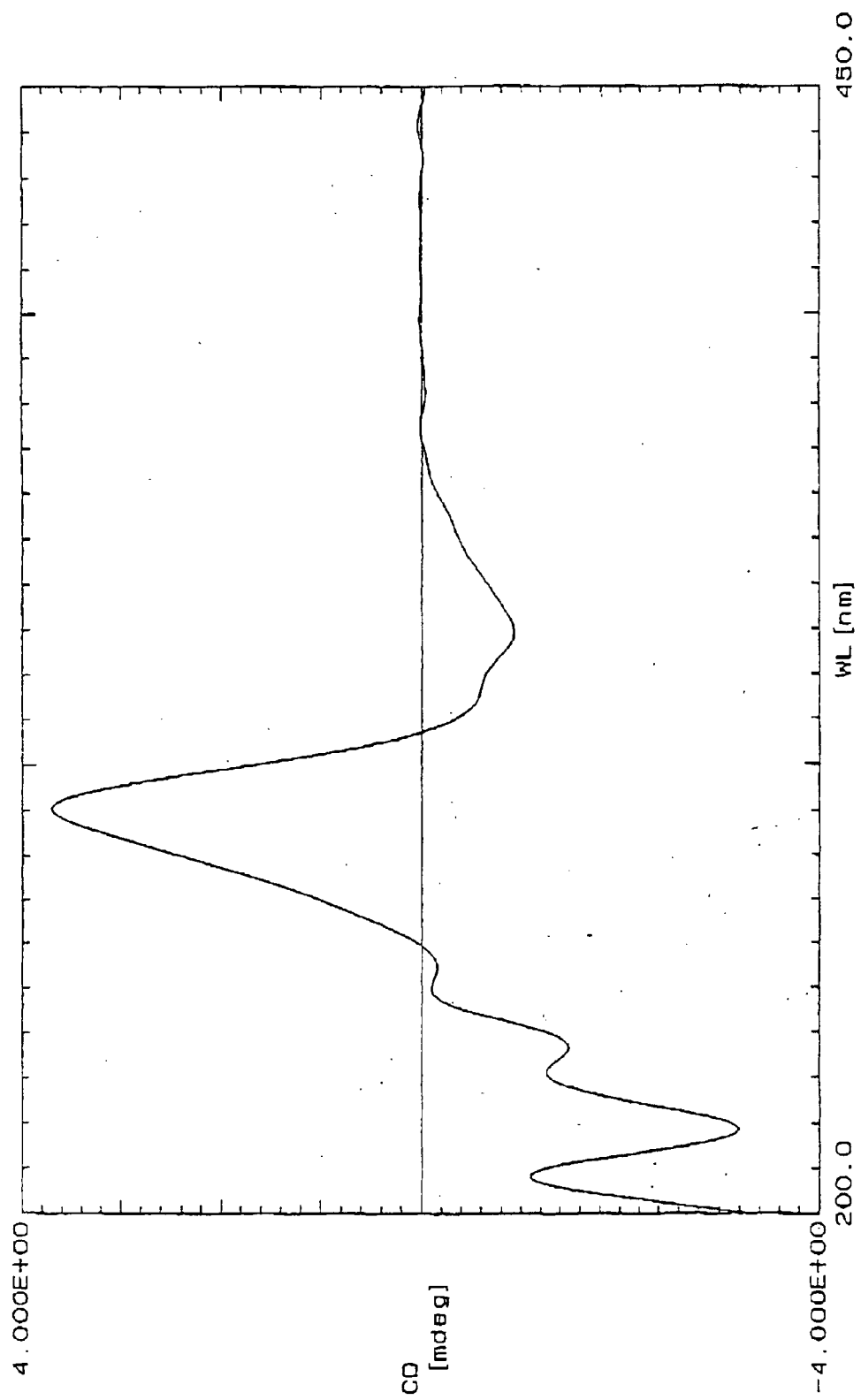
FIG. 10 shows a circular dichroism (CD) spectrum of the compound contained in the lyophilizate of the 7th (No. 7) peak.

FIG. 10 shows a circular dichroism spectrum (CD) of the compound contained in the lyophilizate of the 7th (No. 7) peak. It is understood that the strong positive Cotton effect at around 290 nm and the weak negative Cotton effect at around 230 nm are attributed to π→π* and n→π* transitions, respectively due to UV absorption bands corresponding thereto. By comparing the sign of these Cotton effects with those described in a literature (W. Gaffield, Tetrahedron, 26, 4093–4108 (1970)), the absolute configuration at the 2 position in the flavanone skeleton was determined as (R).

In addition, the compound contained in the lyophilizate of the 7th (No. 7) peak was analyzed by $^1$H-NMR and $^1$H-$^{13}$C correlation two-dimensional NMR (HMBC, HSQC). The results are shown in FIG. 11 as well as FIGS. 12 and 13, respectively.

Figure 11:
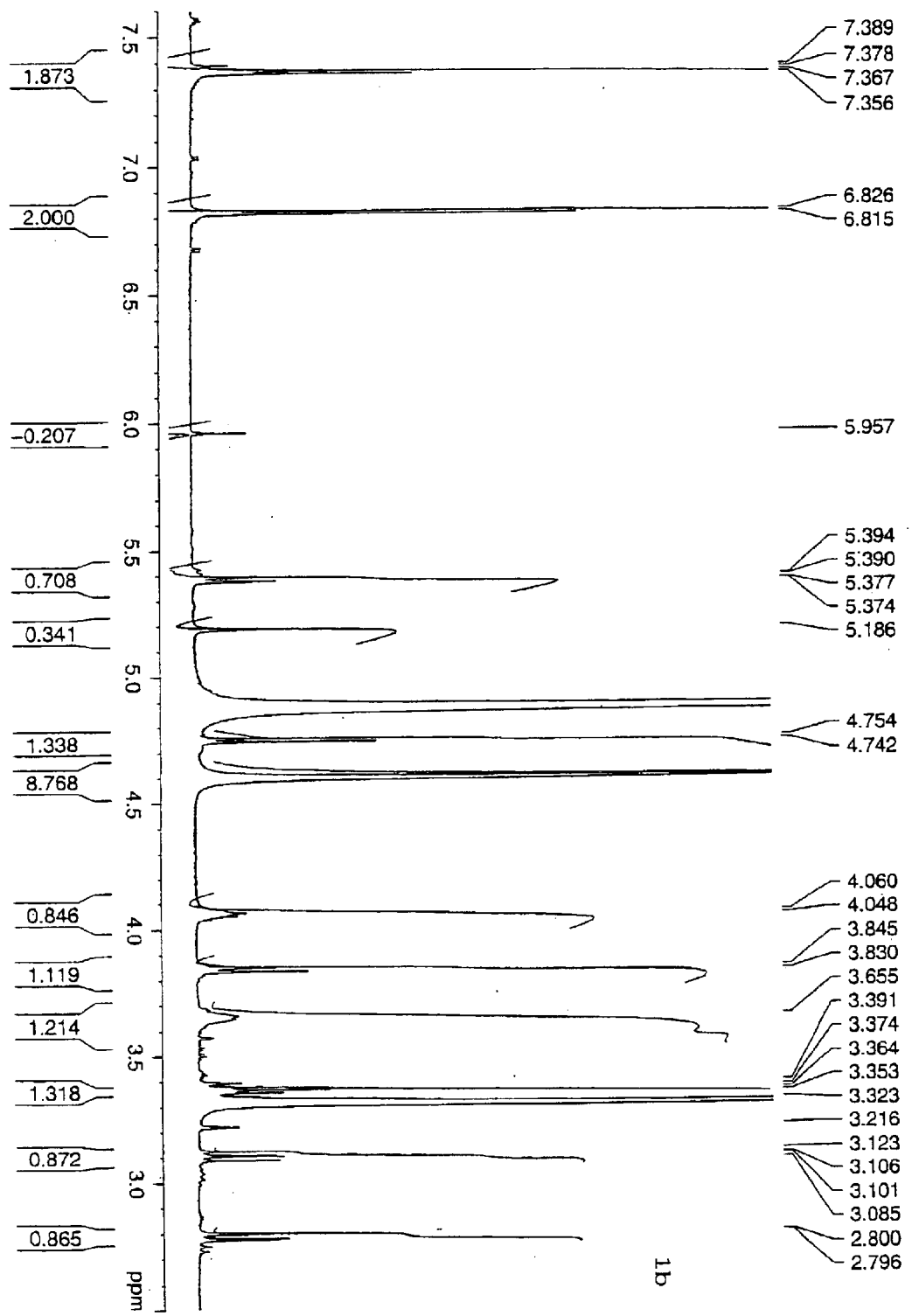
FIG. 11 shows a $^1$H-NMR spectrum of the compound contained in the lyophilizate of the 7th (No. 7) peak.
Figure 12:
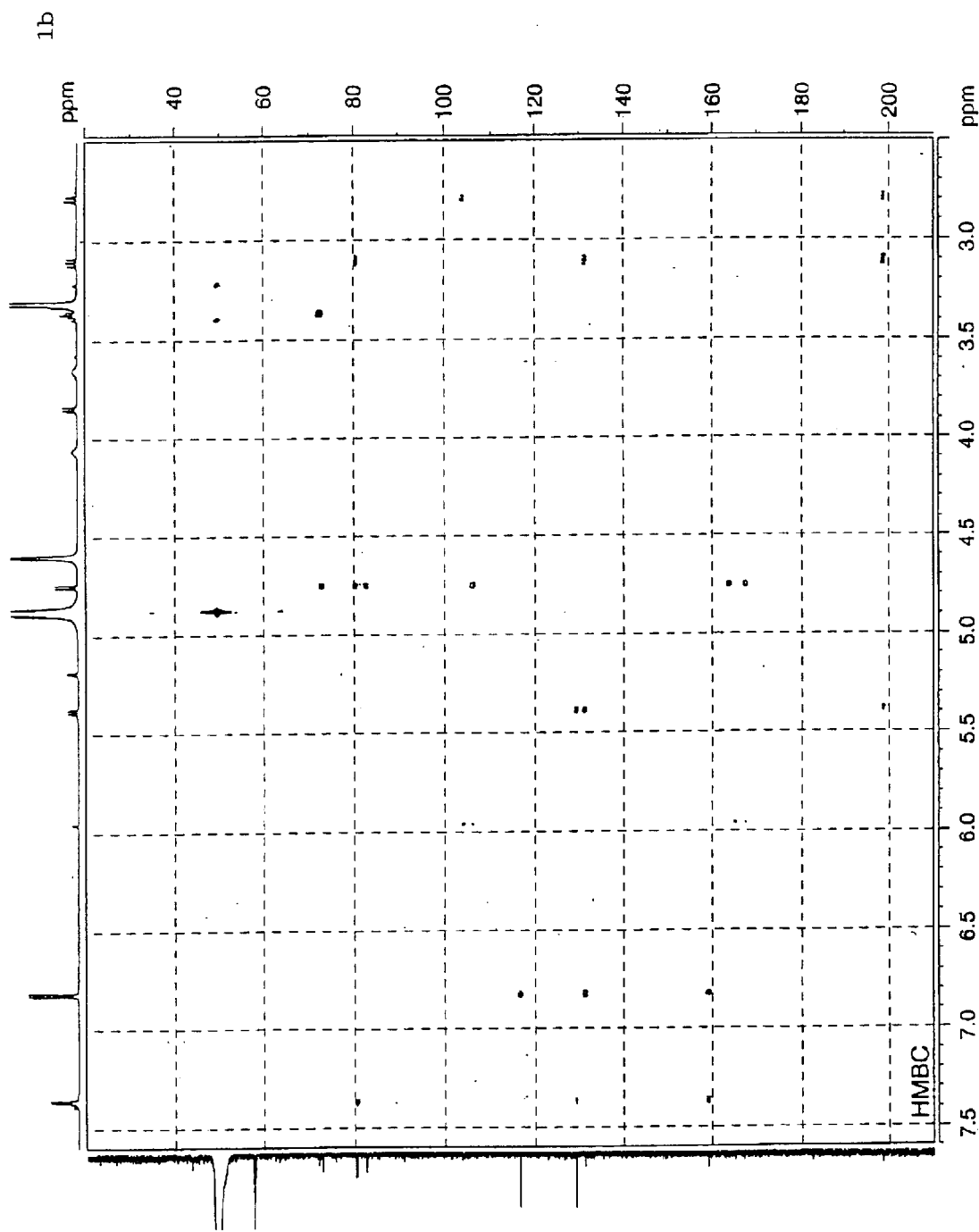
FIG. 12 shows a $^1$H-$^{13}$C HMBC correlation two-dimensional NMR spectrum of the compound contained in the lyophilizate of the 7th (No. 7) peak.
Figure 13:
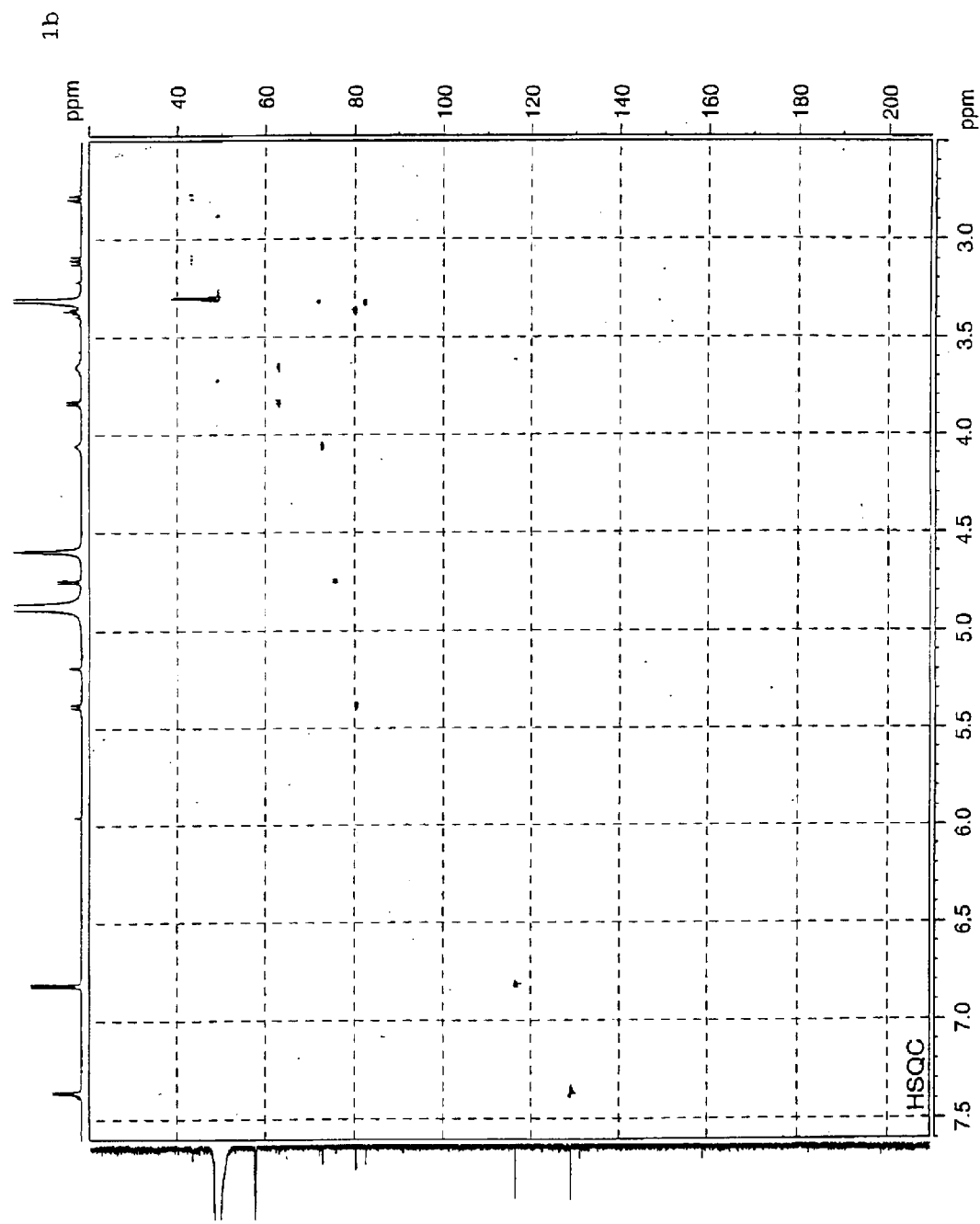
FIG. 13 shows a $^1$H-$^{13}$C HSQC correlation two-dimensional NMR spectrum of the compound contained in the lyophilizate of the 7th (No. 7) peak.

FIG. 11 shows a $^1$H-NMR spectrum of the compound contained in the lyophilizate of the 7th (No. 7) peak. FIG. 12 shows a $^1$H-$^{13}$C HMBC correlation two-dimensional NMR spectrum of the same compound. FIG. 13 shows a $^1$H-$^{13}$C HSQC correlation two-dimensional NMR spectrum of the same compound.

From the results of these analyses, it was found that the compound of the 7th (No. 7) peak is a novel compound 8-C-β-D-glucosyl-(R)-naringenin of the above formula (II) which has not yet been described in any literature.

From the above results, it became clear that the insecticidal substance active to azuki bean weevils contained in the seeds of rice bean is 8-C-β-D-glucosyl-(R)-naringenin, and the present inventors succeeded in isolation and purification thereof.

Example 2
[Production of 6-C-β-D-glucosyl-(R)-naringenin]

In Example 1, the insecticidal substance active to azuki bean weevils, i.e., 8-C-β-D-glucosyl-(R)-naringenin, was separated from rice bean.

The seeds of rice bean, however, also have insect resistance to cowpea weevils as shown in FIG. 1. It is estimated, accordingly, that the seeds may contain another insecticidal substance in addition to 8-C-β-D-glucosyl-(R)-naringenin.

Figure 14:
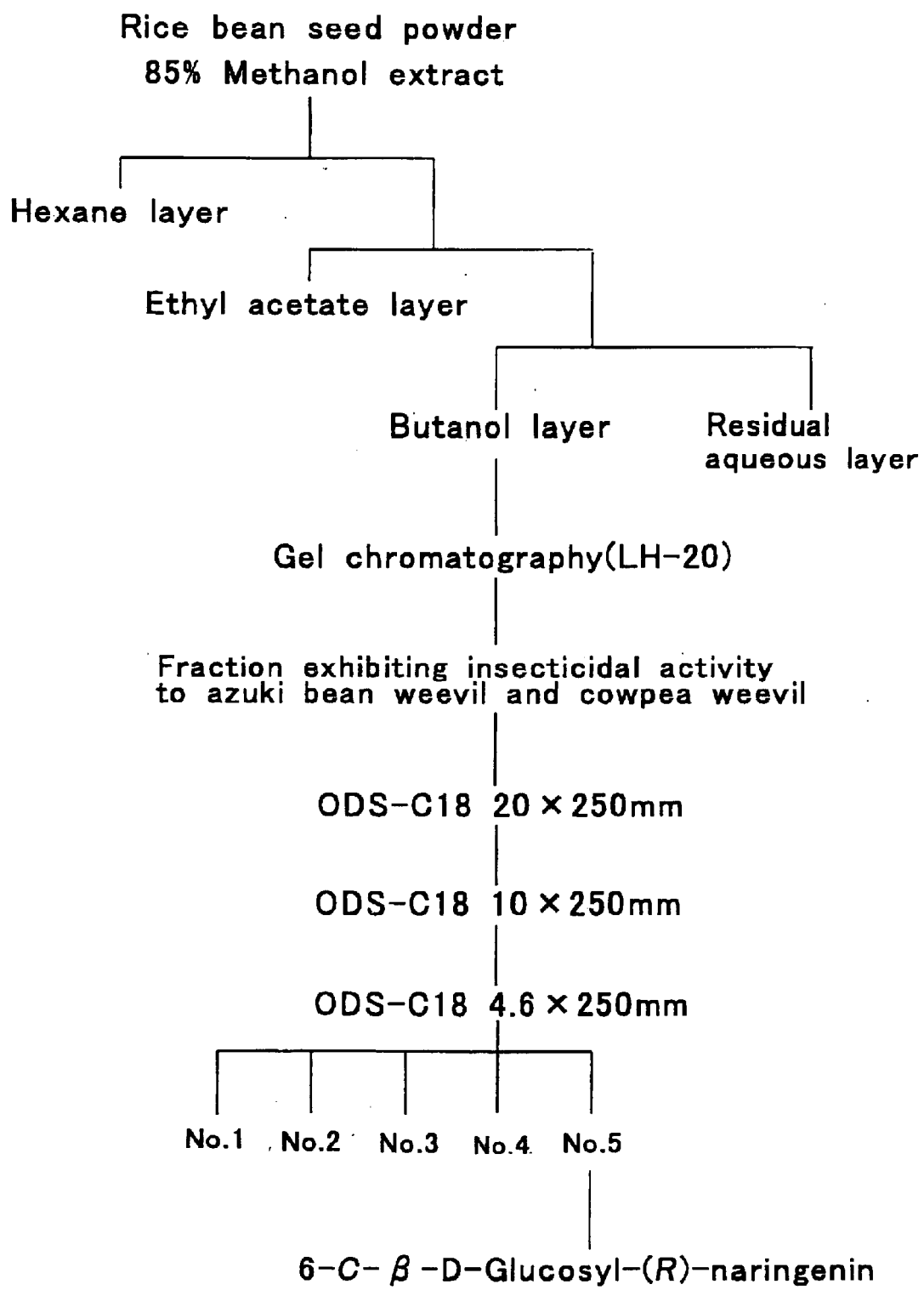
FIG. 14 shows a procedure for separation and purification of 6-C-β-D-glucosyl-(R)-naringenin from the seeds of rice bean.

In Example 1, since the insecticidal activity to cowpea weevils was lost by passing through a silica gel column by chromatography, isolation of an insecticidal substance active to azuki bean weevils and cowpea weevils was attempted without using silica gel. FIG. 14 shows a procedure for separation and purification.

(1) Extraction with Methanol

The seeds of rice bean (1000 g) were pulverized with a high speed grinder. To the pulverized seed powder was added 10 l of 85% methanol (methanol:water=85:15) and extracted continuously for 48 hours (4° C.). The extract was filtered to give 9.5 l of supernatant. This operation was repeated 4 times to obtain about 38 l of methanol extract from total 4000 g of the seed powder.

For the methanol extract, the total activity, specific activity and yield were calculated in the same manner as in Experiment 1. Table 2 shows the results.

From Table 2, it is apparent that the insecticidal activity was improved by extraction with methanol.

(2) Partition to a Variety of Solvents

The methanol extract was condensed and partitioned into water-saturated hexane, ethyl acetate, and water-saturated butanol. The butanol layer was condensed and freeze-dried.

The respective partitioned layers were confirmed to have insecticidal activity to two species of bean weevils.

The artificial beans were prepared by mixing the respective partitioned layers, and the test for the insecticidal activity was carried out in the same manner as in Experiment 1. As a result, the insecticidal activity was recognized in the separated butanol layer. For the separated butanol layer, the total activity and specific activity to two species of bean weevils and the yield are shown in Table 2.

(3) Separation by Gel Chromatography

The lyophilizate of the partitioned butanol layer was dissolved in a small quantity of 10% methanol (methanol/water=10:90). The dissolved specimen was separated on an LH-20 packed column (6×100 cm) for gel chromatography. The column was eluted with 10% methanol as a starting solvent and in a linear concentration gradient up to 100% methanol for 48 hours (flow rate 5 ml/min; column temperature 20° C.). The eluates were collected every 10 minutes, from 120 minutes after addition of a sample. The respective fractions collected were condensed in vacuum. The fractions active against azuki bean weevils and cowpea weevils were identified.

The insecticidal activity to azuki bean weevils and cowpea weevils was confirmed in the respective fractions.

The artificial beans were prepared by mixing the above respective fractions, and the test for the insecticidal activity was carried out in the same manner as in Experiment 1 to calculate the rate of emergence, total activity and specific activity. As a result, a fraction in which the insecticidal activity to two species of bean weevils was recognized was obtained. The total activity, specific activity and yield for the fraction in which the insecticidal activity has been recognized are shown in Table 2.

(4) Separation by HPLC

The fractions in which the insecticidal activity was recognized were purified by HPLC (Shimadzu). The columns Sensyu Kagaku ODS-C18 (20×250 mm and 10×250 mm) and Shiseido ODS-UC18 (4.6×250 mm) were employed. The absorbance was measured at 200 to 400 nm.

Figure 15:
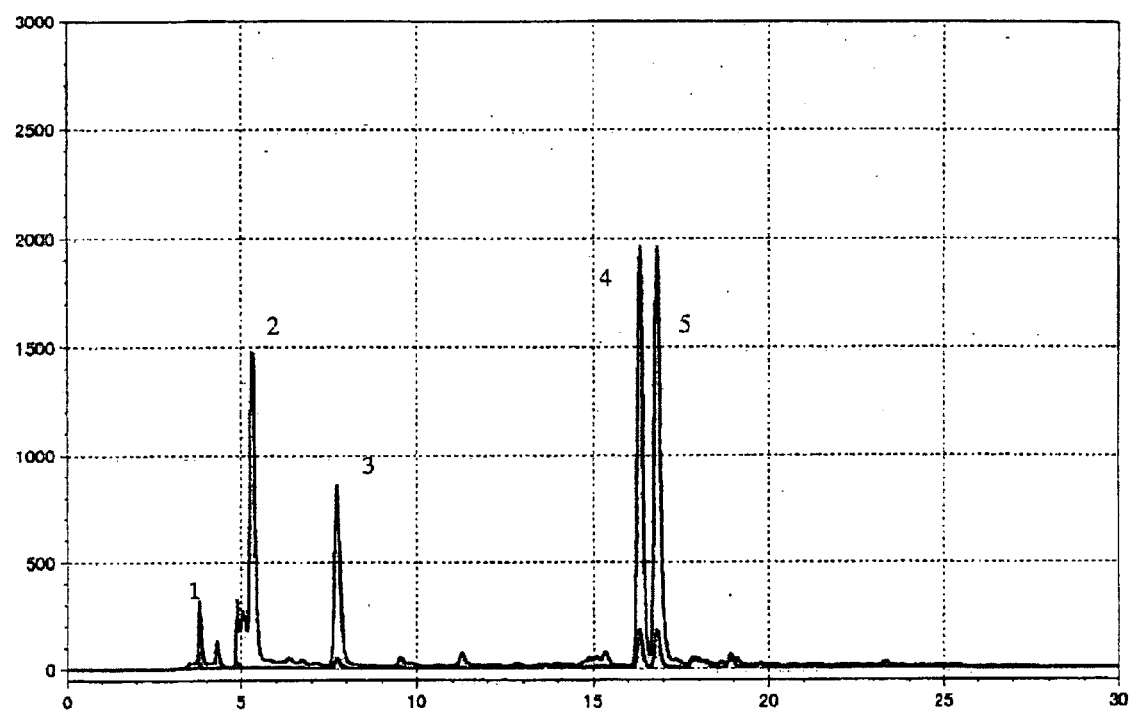
FIG. 15 shows the result of HPLC.

The fractions in which insecticidal activity was recognized to azuki bean weevils and cowpea weevils were analyzed on a column of ODS-UC18 (4.6×250 mm) by eluting with 15% acetonitrile+0.1% formic acid (acetonitrile/water=15:75) at a flow rate of 0.8 ml/min. and a column temperature of 30° C. As a result, 5 peaks (Nos. 1 to 5) were detected as shown in FIG. 15.

Each peak was collected, and its insecticidal activity was confirmed. The artificial beans were prepared by mixing the above respective peaks, and the test for insecticidal activity was carried out in the same manner as in Experiment 1. As a result, insecticidal activity to azuki bean weevils and cowpea weevils was recognized at the peaks appearing at 16 to 17 minutes of the elution time (Nos. 4 and 5).

The peak fractions of 16 to 17 minutes (Nos. 4 and 5) were separated on columns of ODS-C18 (20×250 mm and 10×250 mm).

The insecticidal activity was confirmed for the 5th (No. 5) peak. The insecticidal test was carried out in the same manner as in Experiment 1 to calculate the rate of emergence, except that the artificial beans were prepared by mixing 0.05%, 0.1%, or 0.2% of the 5th (No. 5) peak fraction.

Figure 16:
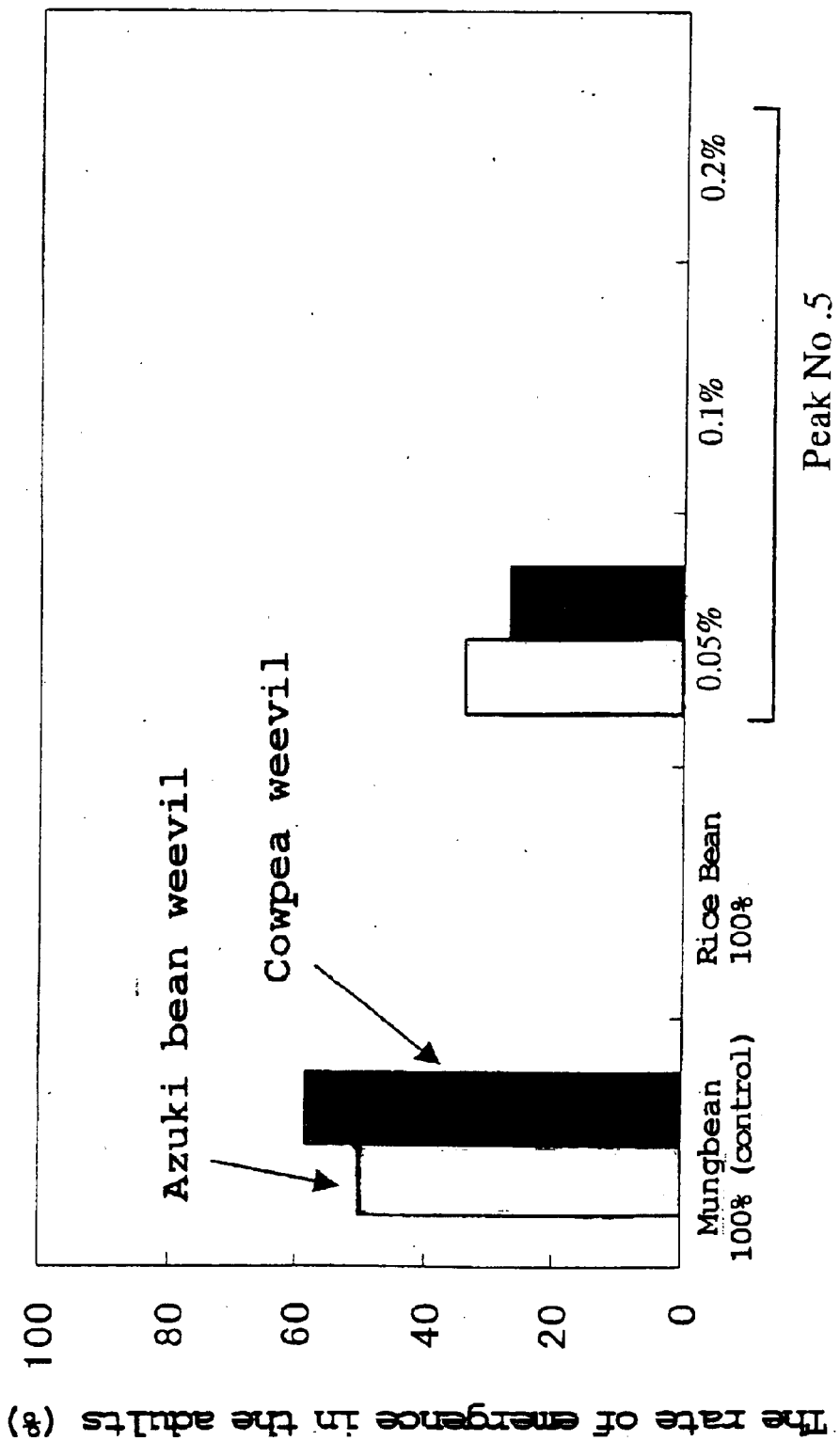
FIG. 16 shows the rate of emergence of adults on the artificial beans prepared by mixing the chemical represented in the 5th (No. 5) peak.

FIG. 16 shows the result of the rate of emergence on the artificial beans containing the 5th (No. 5) peak. In FIG. 16, the white bar indicates the results for azuki bean weevils and the black bar for cowpea weevils, respectively.

As seen clearly from FIG. 16, the rate of weevil emergence on the artificial beans containing the 5th (No. 5) peak extract was low for both two species of bean weevils. On the artificial beans containing 0.1% or 0.2% of the 5th (No. 5) peak, however, the rate of emergence in two species of bean weevils was 0%. Thus, the minimum lethal concentration was confirmed to be 0.1%.

In the same manner as in Experiment 1, the total activity and specific activity were calculated for the artificial beans containing the 5th (No. 5) peak extract. Further, the yield was calculated. The results are shown in Table 2.

TABLE 2

Insecticidal activity of the extract in each step of purification

| Purification step | Extract (g) | Total activity (units) | Specific activity (units/g) | Yield (%) |
|---|---|---|---|---|
| rice bean seed powder | 1000.0 | 1250.0 | 1.3 | 100.0 |
| Methanol extract | 51.5 | 858.3 | 16.7 | 68.7 |
| Butanol partition layer | 15.4 | 513.3 | 33.3 | 41.1 |
| Low pressure liquid chromatography (Active fraction) | 0.8 | 106.7 | 133.3 | 8.5 |
| HPLC (5th peak) | 0.008 | 8.0 | 1000.0 | 0.6 |

As seen from Table 2, in the 5th (No. 5) peak, the total activity is low, and the specific activity is high.

From the above results, since the insecticidal activity to azuki bean weevils and cowpea weevils was recognized in the 5th (No. 5) peak, this peak fraction was analyzed as follows.

Figure 17:
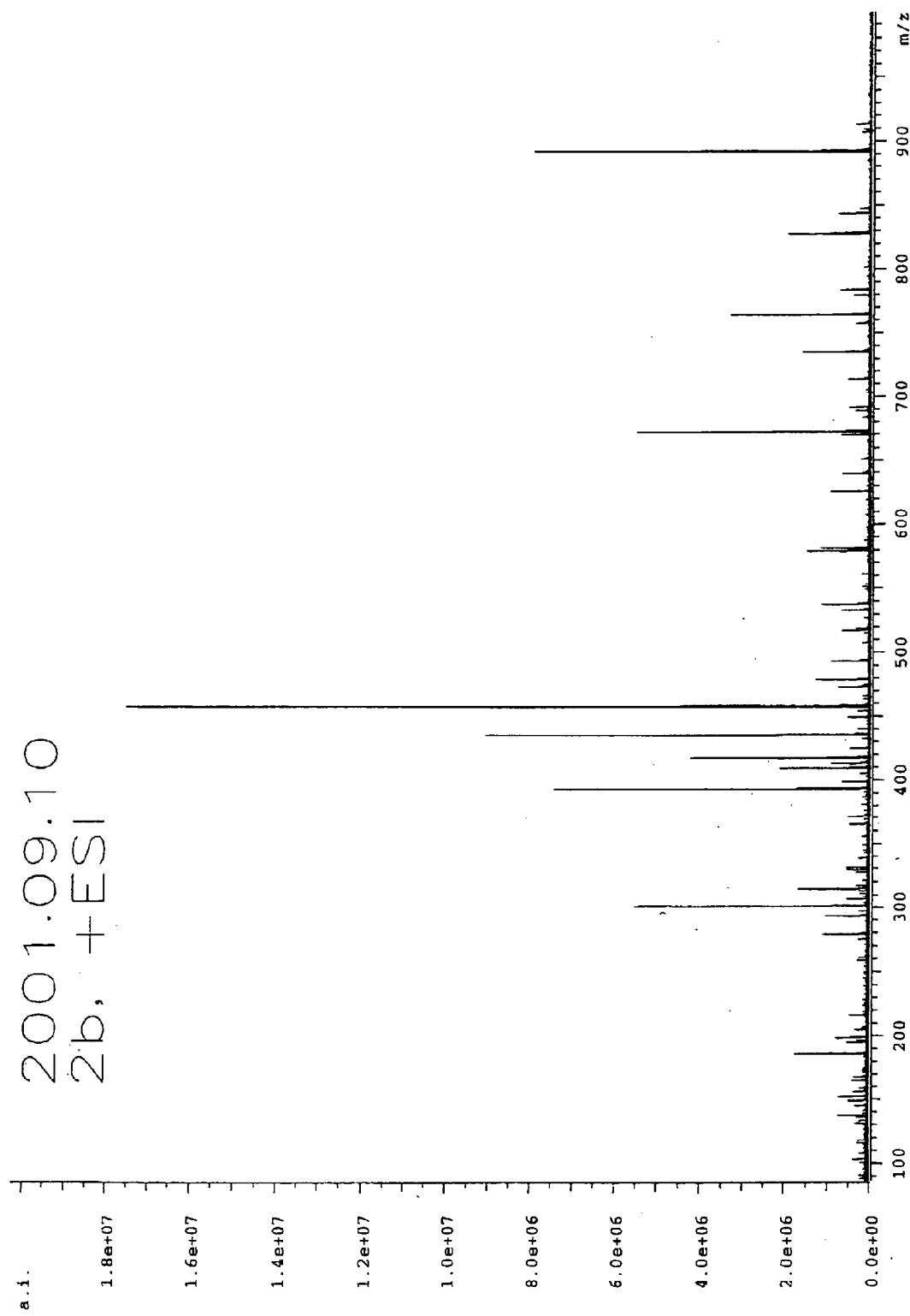
FIG. 17 shows the result of mass spectroscopic analysis (mass spectrum) of the compound contained in the lyophilizate of the 5th (No. 5) peak.
Figure 18:
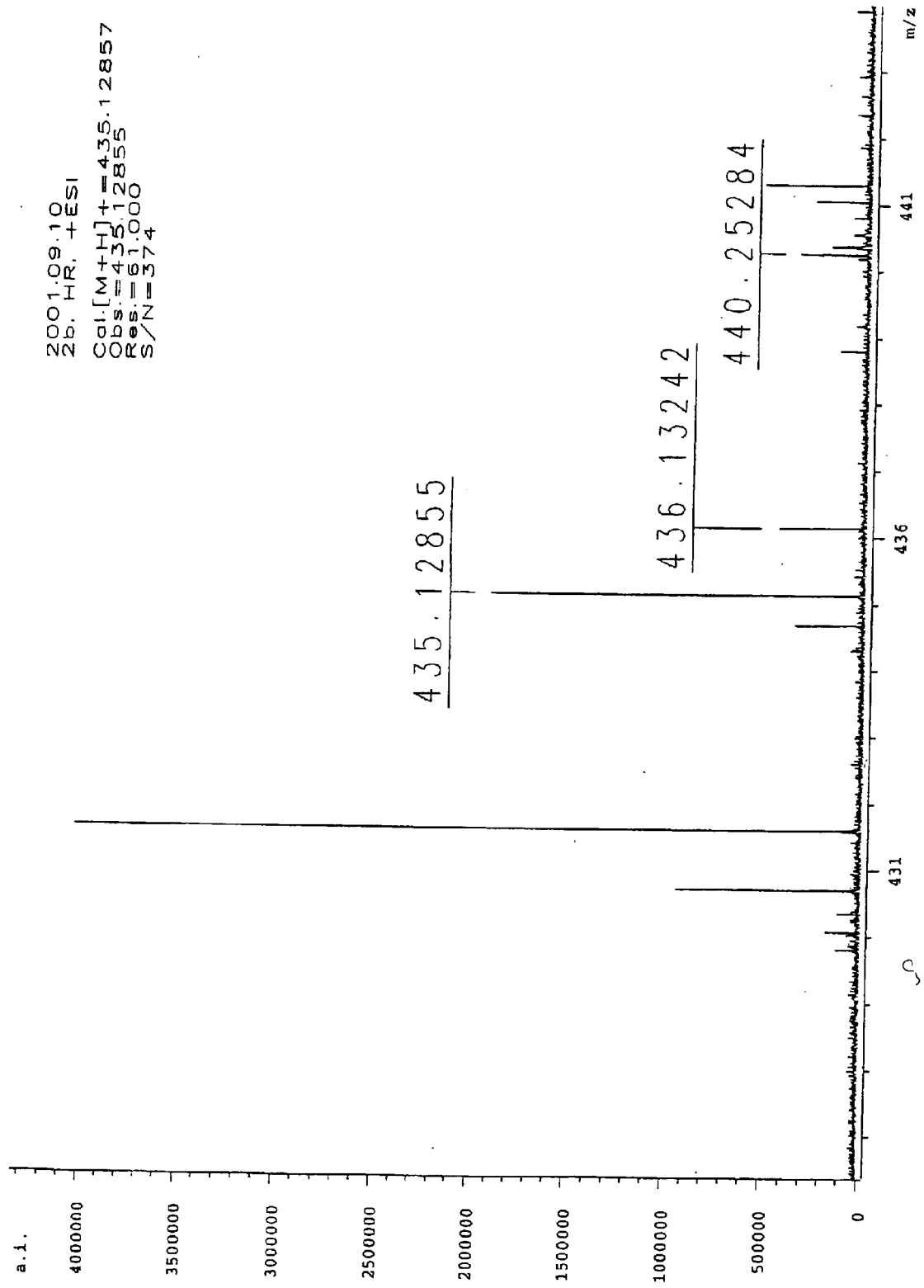
FIG. 18 shows the result of precision mass spectroscopic analysis (mass spectrum: [M+H]$^+$) of the compound contained in the lyophilizate of the 5th (No. 5) peak.
Figure 19:
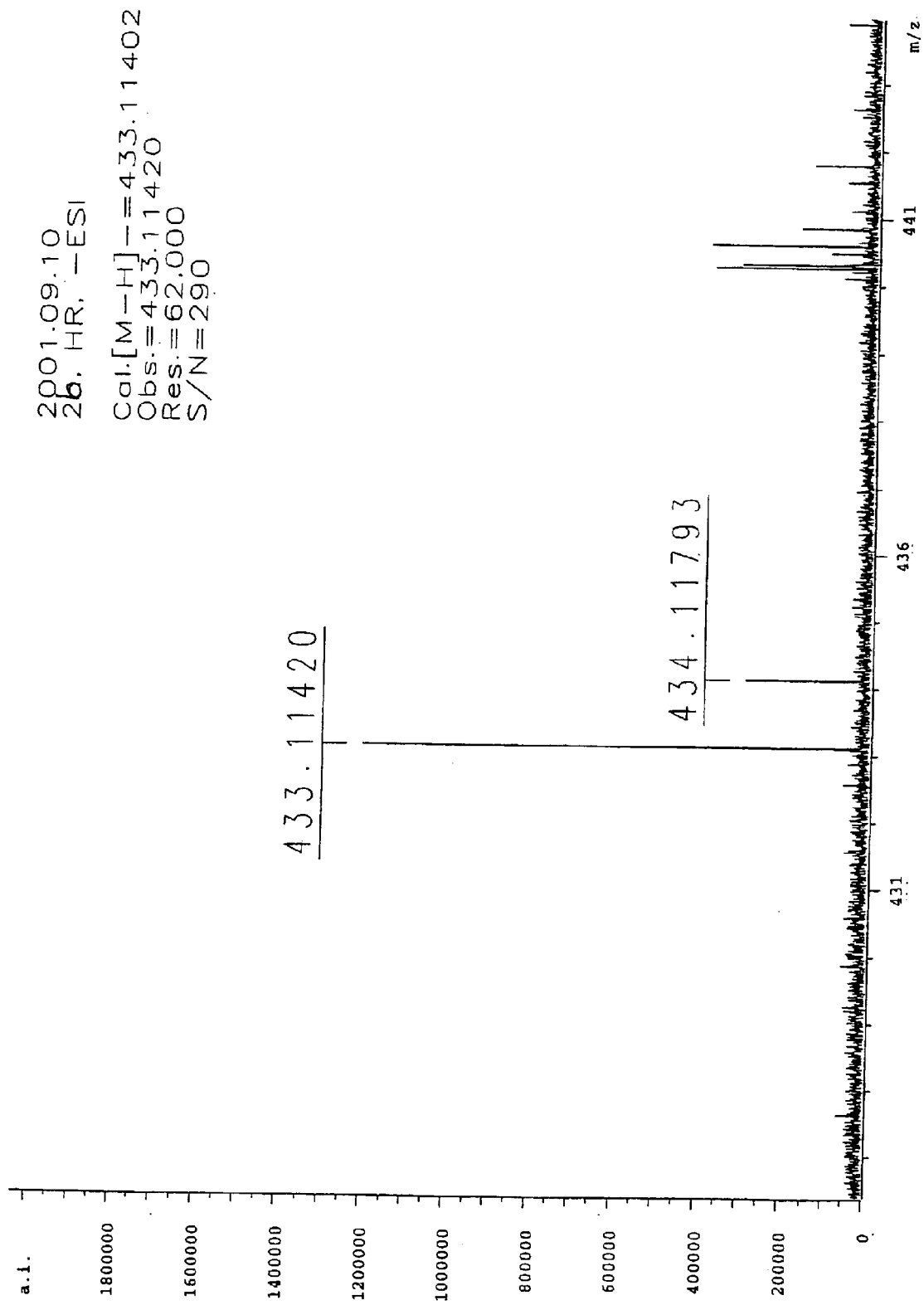
FIG. 19 shows the result of precision mass spectroscopic analysis (mass spectrum: [M–H]$^-$) of the compound contained in the lyophilizate of the 5th (No. 5) peak.

The compound contained in the lyophilizate of the 5th (No. 5) peak fraction was analyzed by the Fourier transformation ion cyclotron resonance mass spectrometry (FTICR-MS). The results of mass spectrometric analyses are shown in FIG. 17 (mass spectra). The results of precision mass spectrometric analyses (precision mass spectra) are shown in FIGS. 18 and 19. As shown in FIGS. 18 and 19, $[M+H]^+$ was observed at m/z 435.12855, and $[M-H]^-$ atm/z433.11420. When regarded as $C_{21}H_{23}O_{10}$, $[M+H]^+$ is m/z 435.12855, and $[M-H]^-$ is m/z 433.11402.

Figure 20:
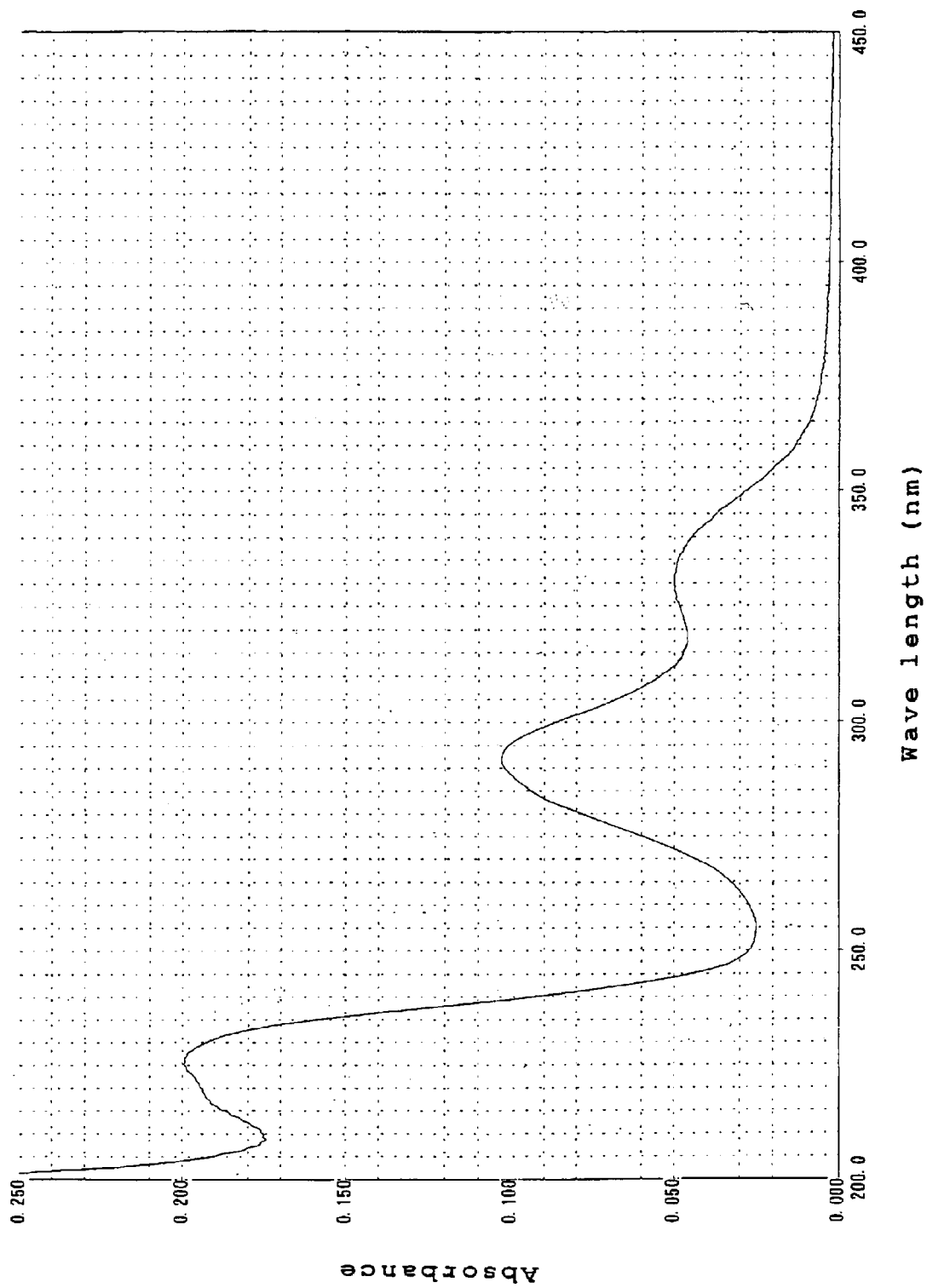
FIG. 20 shows a UV spectrum of the compound contained in the lyophilizate of the 5th (No. 5) peak.

FIG. 20 shows a UV spectrum of the compound contained in the lyophilizate of the 5th (No. 5) peak. The strong absorption band at around 290 nm and the weak absorption band at around 330 nm are attributed to $\pi \rightarrow \pi^*$ and $n \rightarrow \pi^*$ transitions, respectively due to UV absorption bands corresponding thereto, in the flavanone skeleton.

Figure 21:
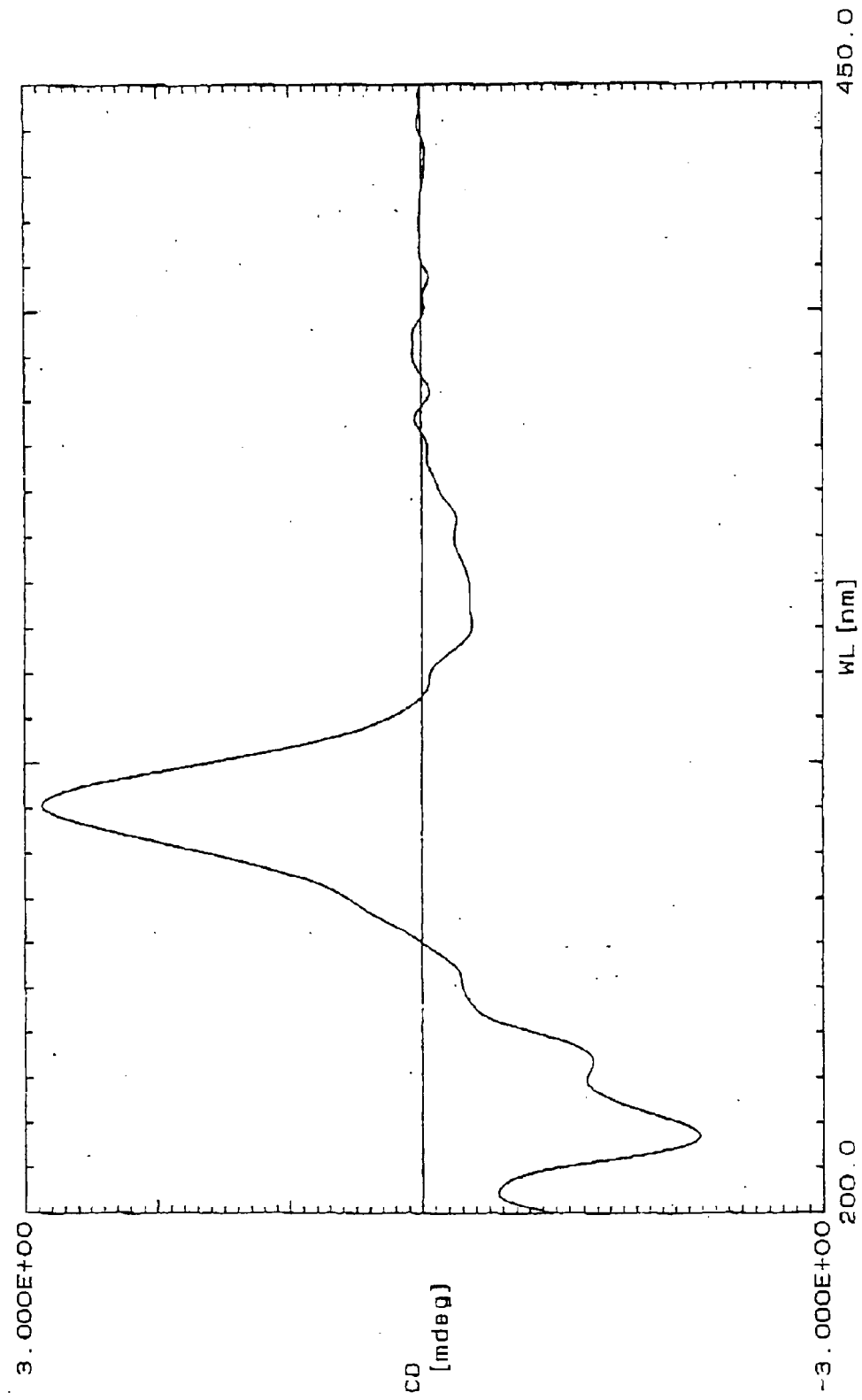
FIG. 21 shows a circular dichroism (CD) spectrum of the compound contained in the lyophilizate of the 5th (No. 5) peak.

FIG. 21 shows a circular dichroism spectrum (CD) of the compound contained in the lyophilizate of the 5th (No. 5) peak. It is understood that the strong positive Cotton effect at around 290 nm and the weak negative Cotton effect at around 230 nm are attributed to $\pi \rightarrow \pi^*$ and $n \rightarrow \pi^*$ transitions, respectively. By comparing the sign of these Cotton effects with those described in a literature (W. Gaffield, Tetrahedron, 26, 4093–4108 (1970)), the absolute configuration at the 2 position in the flavanone skeleton was determined as (R).

In addition, the compound contained in the lyophilizate of the 5th (No. 5) peak was analyzed by $^1$H-NMR, $^{13}$C-NMR and $^1$H-$^{13}$C correlation two-dimensional NMR (HMBC, HSQC). The results are shown in FIGS. 22 and 23 as well as FIGS. 24 and 25, respectively.

Figure 22:
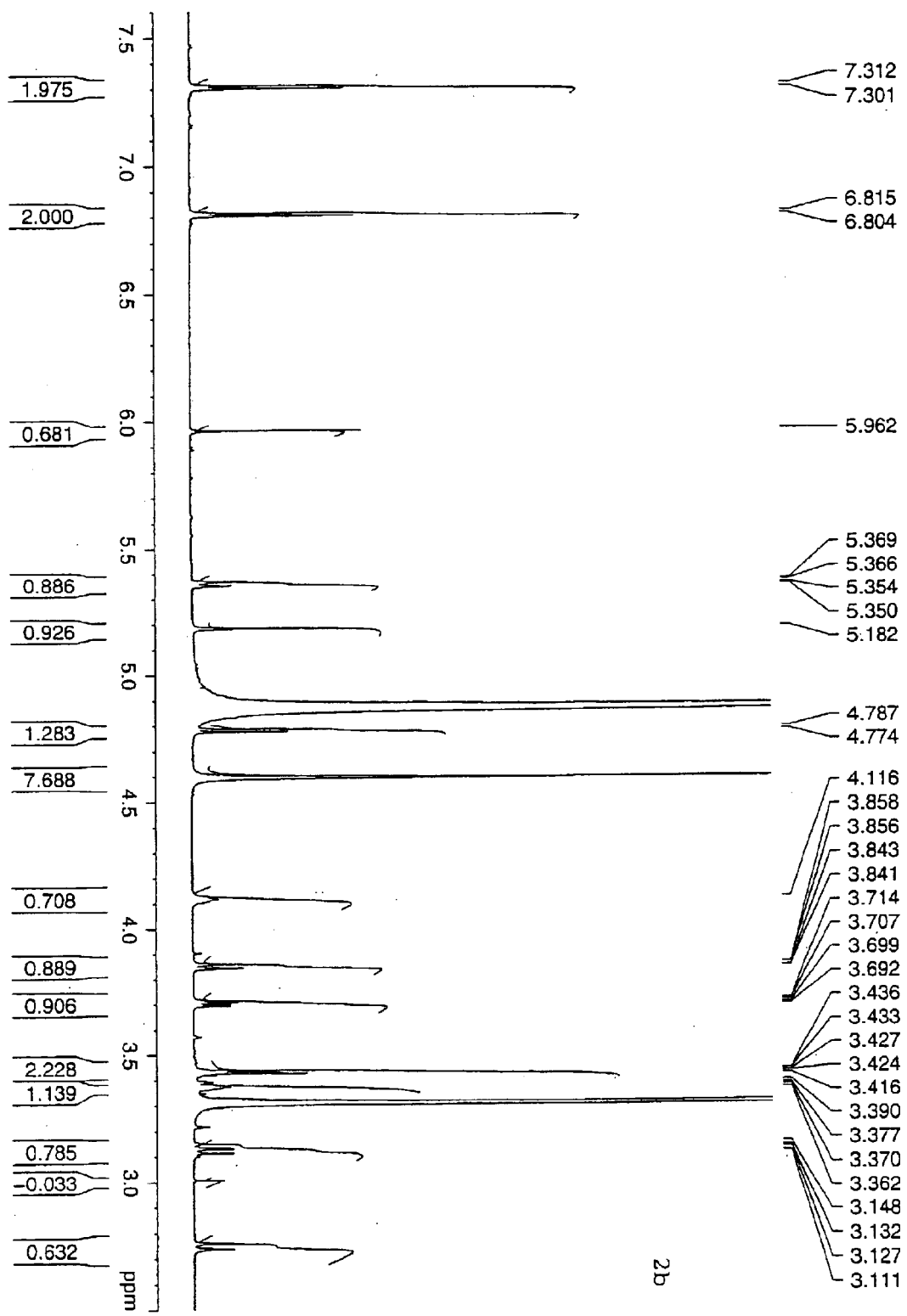
FIG. 22 shows a $^1$H-NMR spectrum of the compound contained in the lyophilizate of the 5th (No. 5) peak.
Figure 23:
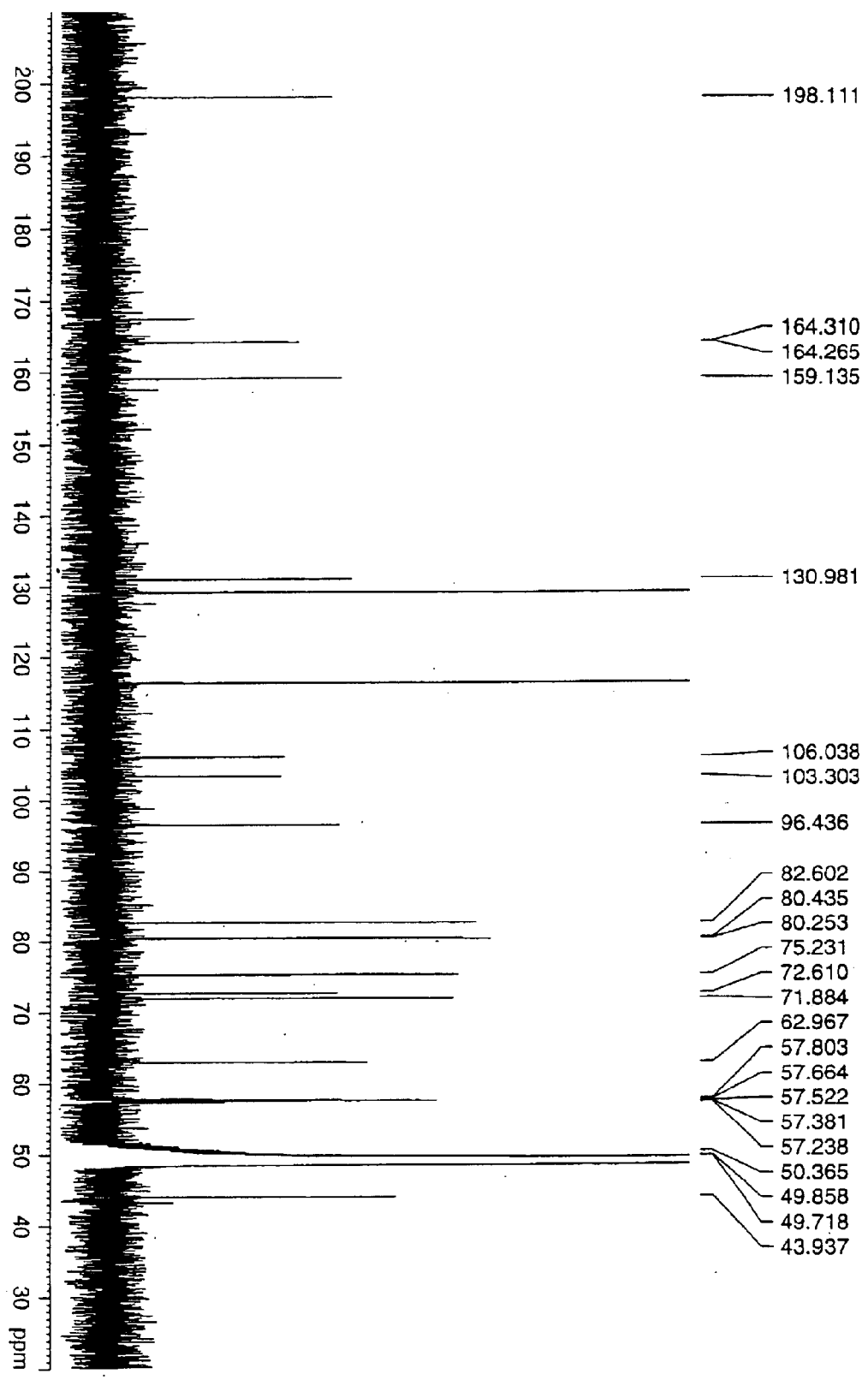
FIG. 23 shows a $^{13}$C-NMR spectrum of the compound contained in the lyophilizate of the 5th (No. 5) peak.
Figure 24:
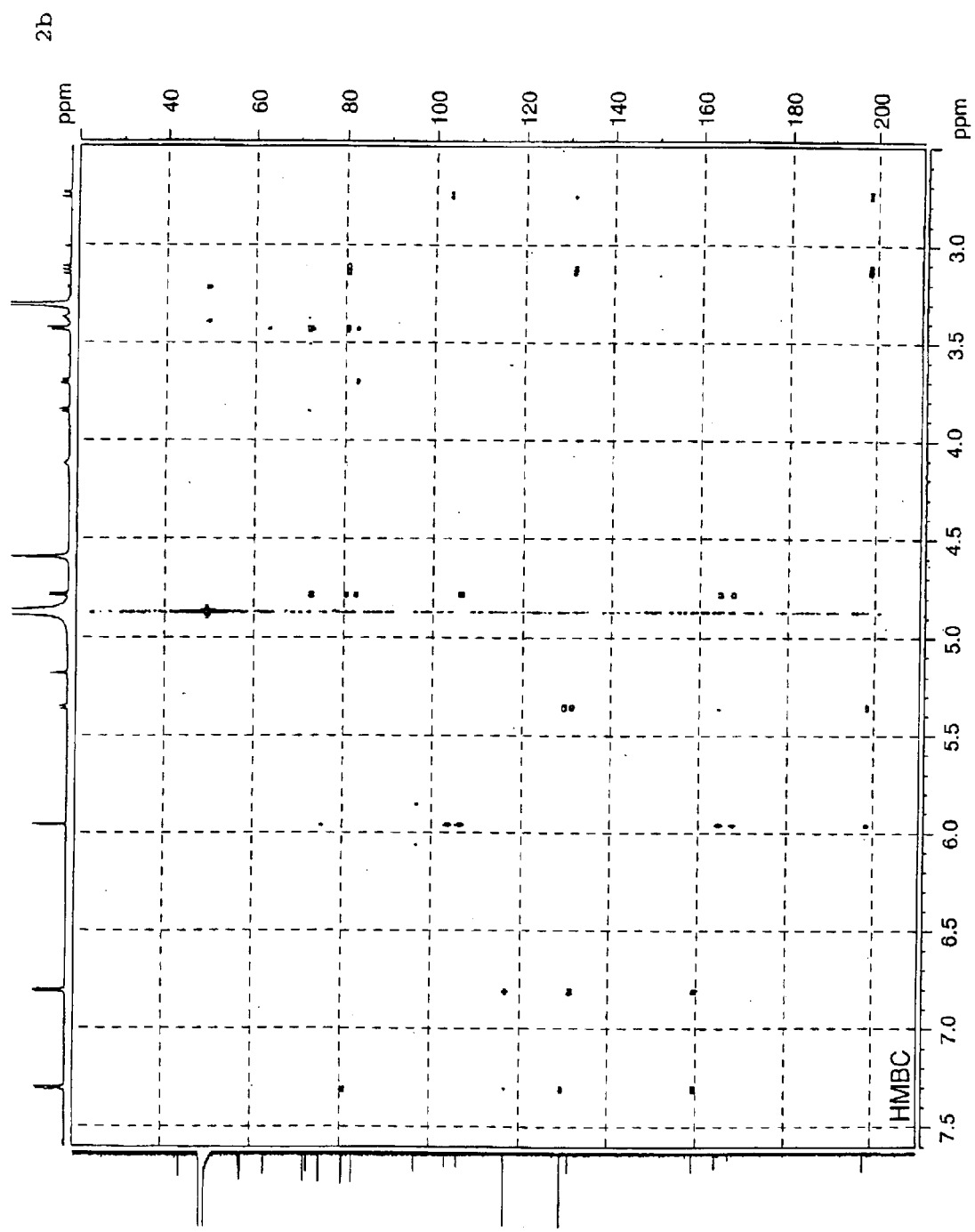
FIG. 24 shows a $^1$H-$^{13}$C HMBC correlation two-dimensional NMR spectrum of the compound contained in the lyophilizate of the 5th (No. 5) peak.
Figure 25:
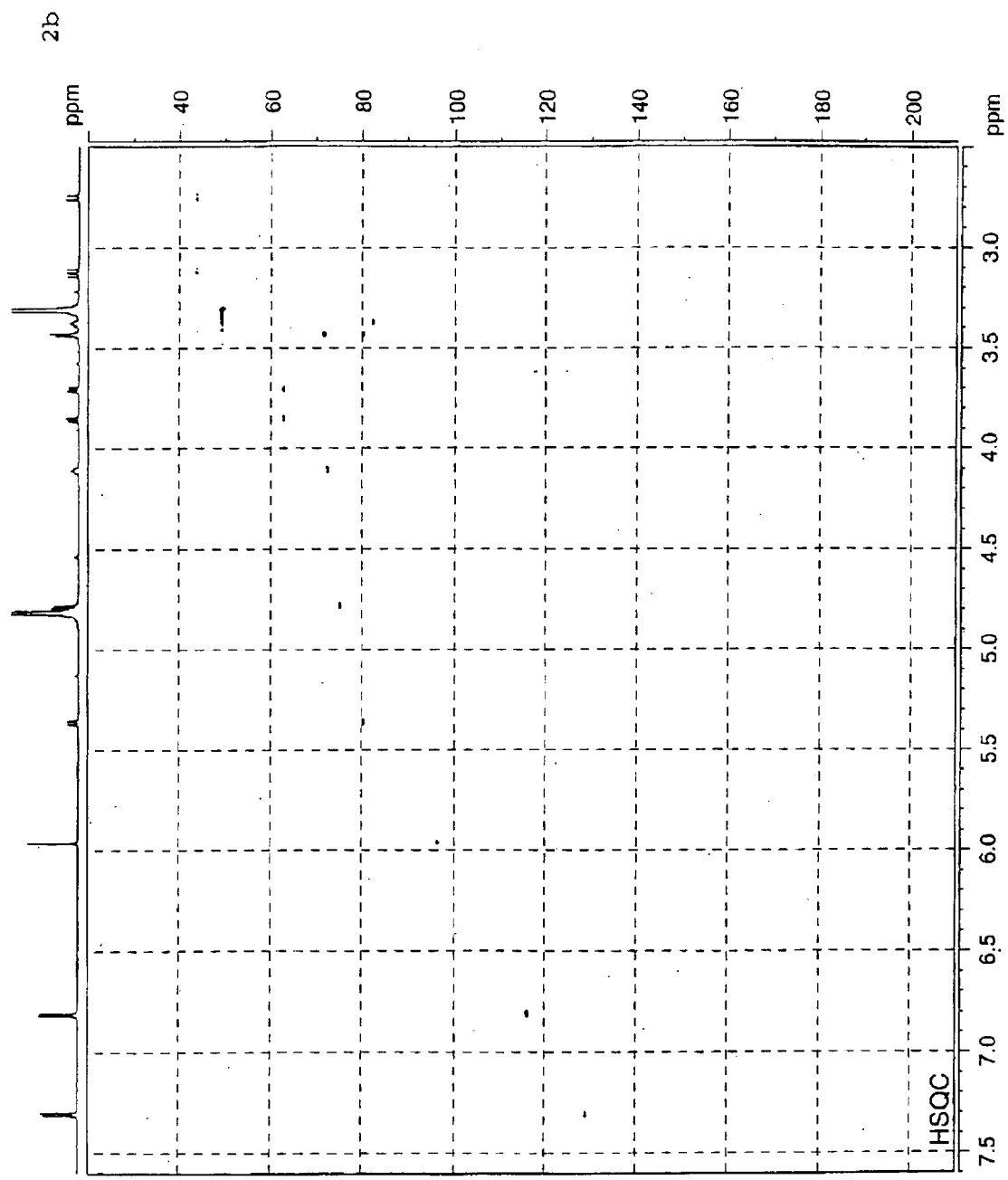
FIG. 25 shows a $^1$H-$^{13}$C HSQC correlation two-dimensional NMR spectrum of the compound contained in the lyophilizate of the 5th (No. 5) peak.

FIG. 22 shows a $^1$H-NMR spectrum of the compound contained in the lyophilizate of the 5th (No. 5) peak. FIG. 23 shows a $^{13}$C-NMR spectrum of the same compound. FIG. 24 shows a $^1$H-$^{13}$C HMBC correlation two-dimensional NMR spectrum of the same compound. FIG. 25 shows a $^1$H-$^{13}$C HSQC correlation two-dimensional NMR spectrum of the same compound.

From the results of these analyses, it was found that the compound of the 5th (No. 5) peak is a novel compound 6-C-β-D-glucosyl-(R)-naringenin of the above formula (III) which has not yet been described in any literature.

From the above results, it became clear that the insecticidal substance active to azuki bean weevils and cowpea weevils, which is contained in the seeds of rice bean, is 6-C-β-D-glucosyl-(R)-naringenin.

What is claimed is:

1. A naringenin derivative of the general formula I:

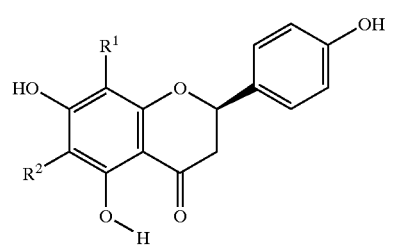

(I)

wherein $R^1$ and $R^2$ each represents either a hydrogen atom or β-D-glucosyl group, but both $R^1$ and $R^2$ are not identical.

2. An insecticidal composition comprising the naringenin derivative of claim 1 as an active component and an agriculturally acceptable carrier.

3. A method of preparing the insecticidal composition as claimed in claim 2 comprising, contacting the naringenin derivative with the an agriculturally acceptable carrier.

4. A method of causing at least one injury to at least one insect feeding on at least one legume seed comprising, contacting the composition as claimed in claim 2 with the insect or the legume seed.

5. The method according to claim 4, wherein the insect is a bean weevil.

6. A method of causing at least one injury to at least one insect feeding on at least one legume seed comprising, contacting the naringenin derivative according to claim 1 with the insect or the legume seed.

7. The method according to claim 6, wherein the insect is a bean weevil.

8. The method according to claim 6, wherein the legume seed is rice bean.

9. The naringenin derivative according to claim 1, wherein the derivative is obtained by extracting a seed or a seed powder with a solvent and isolating the naringenin derivative.

10. The naringenin derivative according to claim 1, wherein the derivative is purified by separating the naringenin derivative from a naturally occurring material.

* * * * *